US006403585B1

United States Patent
Vazquez et al.

(10) Patent No.: US 6,403,585 B1
(45) Date of Patent: *Jun. 11, 2002

(54) α-AND β-AMINO ACID HYDROXYETHYLAMINO SULFONYL UREA DERIVATIVES USEFUL AS RETROVIRAL PROTEASE INHIBITORS

(75) Inventors: Michael L. Vazquez, Gurnee; Richard A. Mueller, Glencoe, both of IL (US); John J. Talley; Daniel P. Getman, both of Chesterfield, MO (US); Gary A. DeCrescenzo, St. Peters, MO (US); Eric T. Sun, San Diego, CA (US)

(73) Assignee: G. D. Searle & Co., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/731,911

(22) Filed: Dec. 8, 2000

Related U.S. Application Data

(63) Continuation of application No. 09/345,739, filed on Jul. 1, 1999, now Pat. No. 6,211,176, which is a continuation of application No. 08/709,609, filed on Sep. 6, 1996, now Pat. No. 6,022,872, which is a continuation of application No. 07/968,712, filed on Oct. 30, 1992, now Pat. No. 5,578,606.

(51) Int. Cl.$^7$ .................... A61K 31/535; C07D 265/30; C07D 211/26; C07D 207/04; C07C 255/03

(52) U.S. Cl. .................... 514/237.8; 514/299; 514/252; 514/315; 514/408; 514/521; 544/160; 544/398; 544/400; 546/184; 546/246; 548/578; 558/437

(58) Field of Search ................ 544/160, 398, 544/400; 546/184, 246; 548/578; 558/437; 514/315, 237.8, 299, 408, 252.12, 521

(56) References Cited

U.S. PATENT DOCUMENTS

| | | | |
|---|---|---|---|
| 4,450,164 A | 5/1984 | Bristol et al. | 424/256 |
| 4,477,441 A | 10/1984 | Boger et al. | 424/177 |
| 4,514,391 A | 4/1985 | Gordon et al. | 514/2 |
| 4,548,926 A | 10/1985 | Matsueda et al. | 514/19 |
| 4,599,198 A | 7/1986 | Hoover | 260/998.2 |
| 4,616,088 A | 10/1986 | Ryono et al. | 546/336 |
| 4,668,769 A | 5/1987 | Hoover | 530/331 |
| 4,668,770 A | 5/1987 | Boger et al. | 530/331 |
| 4,757,050 A | 7/1988 | Natarajan et al. | 514/18 |
| 4,880,938 A | 11/1989 | Freidinger | 548/492 |
| H725 H | 1/1990 | Gordon | 548/533 |
| 4,963,530 A | 10/1990 | Hemmi et al. | 514/19 |
| 4,977,277 A | 12/1990 | Rosenberg et al. | 549/215 |
| 5,578,606 A * | 11/1996 | Vazquez et al. | 514/314 |
| 6,022,872 A * | 2/2000 | Vazquez et al. | 514/231.2 |
| 6,211,176 B1 * | 4/2001 | Vazquez et al. | 514/237.8 |

FOREIGN PATENT DOCUMENTS

| | | | |
|---|---|---|---|
| AU | A-79823/87 | 4/1988 | C07K/5/06 |
| EP | 104041 | 3/1984 | C07C/103/52 |
| EP | 114993 | 8/1984 | C07C/103/52 |
| EP | 172347 | 2/1986 | C07K/5/00 |
| EP | 223437 | 5/1987 | C07K/5/00 |
| EP | 0 264 795 | 4/1988 | C07K/5/00 |
| EP | 337714 | 10/1989 | C07K/5/02 |
| EP | 0 342 541 | 11/1989 | C07K/5/02 |
| EP | 0 346 847 | 12/1989 | C07D/207/10 |
| EP | 356223 | 2/1990 | C07K/37/64 |
| EP | 389898 A2 | 10/1990 | C07K/5/02 |
| EP | 389898 A3 | 10/1990 | C07K/5/02 |
| EP | 393445 | 10/1990 | A61K/37/64 |
| EP | 393457 | 10/1990 | C07K/5/06 |
| EP | 402646 | 12/1990 | C07D/213/40 |
| GB | 2184730 | 7/1987 | C07K/5/00 |
| GB | 2200115 | 7/1988 | C07C/103/00 |
| GB | 2209752 | 5/1989 | C07C/103/30 |
| WO | WO84/03044 | 8/1984 | A61K/37/64 |

OTHER PUBLICATIONS

Roberts et al, "Rational Design of Peptide–based Proteinase Inhibitors," Science, 248, 358 (1990).
Erickson et al, "Design Activity, and 2.8Å Crystal Structure of a $C_2$ Symmetric Inhibitor Complexed to HIV–1 Protease," Science, 249, 527 (1990).
Pearl et al, "Sequence specificity of retroviral proteases" Nature, 328, p. 482 (1987).
Martin, Drugs of the Future, 16(3), 210–212 (1991).
Meek et al, *Letter To Nature*, 343, 90–92 (1990).
McQuade et al, *Science*, 274, 454–456 (1990).
Rosenberg et al, *J. Med. Chem.*, 30, 1224–1228 (1987).

* cited by examiner

Primary Examiner—Floyd D. Higel
Assistant Examiner—Ebenezer Sackey
(74) Attorney, Agent, or Firm—Banner & Witcoff, Ltd.

(57) ABSTRACT

α- and β-amino acid hydroxyethylamino sulfonyl urea derivative compounds are effective as retroviral protease inhibitors, and in particular as inhibitors of HIV protease.

7 Claims, No Drawings

α-AND β-AMINO ACID HYDROXYETHYLAMINO SULFONYL UREA DERIVATIVES USEFUL AS RETROVIRAL PROTEASE INHIBITORS

This application is a continuation of application Ser. No. 09/345,739 filed Jul. 1, 1999 now U.S. Pat. No. 6,211,176, which is a continuation of application Ser. No. 08/709,069 filed Sep. 6, 1996, now U.S. Pat. No. 6,022,872, which in turn is a continuation of application Ser. No. 07/968,712 filed Oct. 30, 1992, now U.S. Pat. No. 5,578,606.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to sulfonyl urea derivatives of hydroxyethylamine protease inhibitor compounds, a composition and method for inhibiting retroviral proteases such as human immunodeficiency virus (HIV) protease and for treating a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition may involve a transition-state mimetic whereby the retroviral protease is exposed to a mimetic compound which binds to the enzyme in competition with the gag and gag-pol proteins to thereby inhibit replication of structural proteins and, more importantly, the retroviral protease itself. In this manner, retroviral replication proteases can be effectively inhibited.

Several classes of compounds have been proposed, particularly for inhibition of proteases, such as for inhibition of HIV protease. Such compounds include hydroxyethylamine isosteres and reduced amide isosteres. See, for example, EPO 346 847; EPO 342,541; Roberts et al, "Rational Design of Peptide-Based Proteinase Inhibitors, "Science, 248, 358 (1990); and Erickson et al, "Design Activity, and 2.8 Å Crystal Structure of a $C_2$ Symmetric Inhibitor Complexed to HIV-1 Protease," Science, 249, 527 (1990).

Several classes of compounds are known to be useful as inhibitors of the proteolytic enzyme renin. See, for example, U.S. Pat. No. 4,599,198; U.K. 2,184,730; G.B. 2,209,752; EPO 264 795; G.B. 2,200,115 and U.S. SIR H725. Of these, G.B. 2,200,115, GB 2,209,752, EPO 264,795, U.S. SIR H725 and U.S. Pat. No. 4,599,198 disclose urea-containing hydroxyethylamine renin inhibitors. G.B. 2,200,115 also discloses sulfamic acid-containing hydroxyethylamine renin inhibitors, and EP 0264 795 discloses certain sulfamic acid-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as derivatives of hydroxyethylamino sulfonyl urea inhibitor compounds.

DETAILED DESCRIPTION OF THE INVENTION

In accordance with the present invention, there is provided a retroviral protease inhibiting compound of the formula:

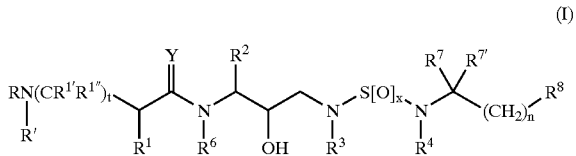

(I)

or a pharmaceutically acceptable salt, prodrug or ester thereof wherein:

R represents hydrogen, alkyl, alkenyl, alkynyl, cycloalkyl, aryl, aralkyl, alkoxycarbonyl, alkoxyalkyl, aryloxyalkyl, heteroaryloxyalkyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or wherein said aminocarbonyl and aminoalkanoyl radicals are disubstituted, said substituents along with the nitrogen atom to which they are attached form a heterocycloalkyl or heteroaryl radical;

R' represents hydrogen, radicals as defined for $R^3$ or R"$SO_2$—wherein R" represents radicals as defined for $R^3$; or R and R' together with the nitrogen to which they are attached represent heterocycloalkyl and heteroaryl radicals;

$R^1$ represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone (SO$_2$) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyanoalanine and valine side chains;

$R^{1'}$ and $R^{1''}$ independently represent hydrogen and radicals as defined for $R^1$, or one of $R^{1'}$ and $R^{1''}$, together with $R^1$ and the carbon atoms to which $R^1$, $R^{1'}$ and $R^{1''}$ are attached, represent a cycloalkyl radical;

$R^2$ represents alkyl, aryl, cycloalkyl, cycloalkylalkyl and aralkyl radicals, which radicals are optionally substituted with a group selected from alkyl and halogen radicals, —NO$_2$, —CN, —CF$_3$, —OR$^9$ and —SR$^9$, wherein $R^9$ represents hydrogen and alkyl radicals, and halogen radicals;

$R^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals or the sulfone or sulfoxide derivatives thereof;

$R^4$ represents hydrogen and radicals as defined by $R^3$;

$R^6$ represents hydrogen and alkyl radicals;

$R^7$ and $R^{7'}$, independently represent hydrogen and radicals as defined for $R^3$; amino acid side chains selected from the group consisting of valine, isoleucine, glycine, alanine, allo-isoleucine, asparagine, leucine, glutamine, and t-butylglycine; radicals represented by the formulas —C(O)R$^{16}$, —CO$_2$R$^{16}$, —SO$_2$R$^{16}$, —SR$^{16}$, —CONR$^{16}$R$^{17}$, —CF$_3$ and —NR$^{16}$R$^{17}$; or $R^7$ and $R^{7'}$, together with the carbon atom to which they are attached form a cycloalkyl radical;

$R^8$ represents cyano, hydroxyl, alkyl, alkoxy, cycloalkyl, aryl, aralkyl, heterocycloalkyl and heteroaryl radicals and radicals represented by the formulas C(O)R$^{16}$, CO$_2$R$^{16}$, SO$_2$R$^{16}$, SR$^{16}$, CONR$^{16}$R$^{17}$, CF$_3$ and NR$^{16}$R$^{17}$;

wherein $R^{16}$ and $R^{17}$ independently represent hydrogen and radicals as defined for $R^3$, or $R^{16}$ and $R^{17}$ together with a nitrogen to which they are attached in the formula NR$^{16}$R$^{17}$ represent heterocycloalkyl and heteroaryl radicals;

x represents 1 or 2;

n represents an integer of from 0 to 6;

t represents either 0, 1 or 2; and

Y represents O, S and NR$^{15}$ wherein $R^{15}$ represents hydrogen and radicals as defined for $R^3$.

Examples of compounds of the present invention as defined by Formula I include:

1) 2S-[[(dimethylamino)acetyl]amino]-N-[3-[[[(2-hydroxy-1,1-dimethylethyl)amino]sulfonyl](3-methylbutyl)amino]-2R-hydroxy-1S-(phenylmethyl)-propyl]-3,3-dimethylbutanamide
2) N-[[[3S-[[2S-[[(dimethylamino)acetyl]amino]-3,3-dimethyl-1-oxobutyl]amino]-2R-hydroxy-4-phenylbutyl](3-methylbutyl)amino]sulfonyl]-2-methylalanine
3) N-[[[3S-[[2S-[[(dimethylamino)acetyl]amino]-3,3-dimethyl-1-oxobutyl]amino]-2R-hydroxy-4-phenylbutyl](3-methylbutyl)amino]sulfonyl]-2-methylalanine, methyl ester
4) 1-[[[[3S-[[2S-[[(dimethylamino)acetyl]amino]-3,3-dimethyl-1-oxobutyl]amino]-2R-hydroxy-4-phenylbutyl](4-pyridinylmethyl)amino]sulfonyl]-amino]cyclopentanecarboxylic acid
5) N-[[[3S-[[4-amino-1,4-dioxo-2S-[(2-quinolinylcarbonyl)amino]butyl]amino]-2R-hydroxy-4-phenylbutyl](2-methylpropyl))amino]sulfonyl]-2-methylalanine
6) 3-[[[[3S-[[2R-[[(dimethylamino)acetyl]amino]-3-methyl-3-(methylthio)-1-oxobutyl]amino]-2R-hydroxy-4-phenylbutyl](2-methylpropyl)amino]sulfonyl]-amino]-3-methylbutanoic acid
7) N-[[[2R-hydroxy-3S-[[3-[[[(4-methoxyphenyl)-methoxy]carbonyl]amino]-2R-methyl-1-oxopropyl]-amino]-4-phenylbutyl(3-methylbutyl)amino]sulfonyl]-2-methylalanine
8) 3-[[[[3S-[[2S-[[(dimethylamino)acetyl]amino]-3-methyl-1-oxopentyl]amino]-2R-hydroxy-4-phenylbutyl][(4-fluorophenyl)methyl]amino]sulfonyl]-amino]-2-methylpropanoic acid
9) 1-[[[[2R-hydroxy-3S-[[3-methyl-1-oxo-2S-[[(phenylmethoxy)carbonyl]amino]butyl]amino]-4-phenylbutyl](3-methylbutyl)amino]sulfonyl]amino]-cyclopentanecarboxylic acid
10) 1-[[[3S-[[4-amino-1,4-dioxo-2S-[(2-quinolinylcarbonyl)amino]butyl]amino]-2R-hydroxy-4-phenylbutyl](3-methylbutyl)amino]sulfonyl]amino]-cyclopropanecarboxylic acid A family of compounds of particular interest within Formula I are compounds embraced by Formula II:

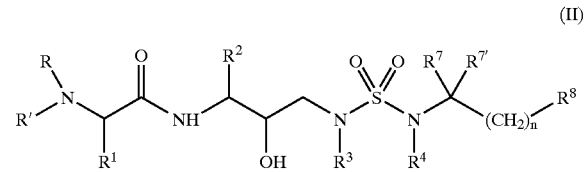

(II)

wherein:

R represents hydrogen, alkyl, alkenyl, cycloalkyl, hydroxyalkyl, aryl, aralkyl, aryloxyalkyl, heteroaryloxyalkyl, alkoxycarbonyl, alkoxyalkyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents hydrogen, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-methyl serine, aspartic acid, beta-cyanoalanine and valine side chains;

$R^2$ represents alkyl, aryl, cycloalkyl, cycloalkylalkyl and aralkyl radicals, which radicals are optionally substituted with a group selected from alkyl and halogen radials; $-NO_2$, $-C\equiv N$, $CF_3$, $-OR^9$, $-SR^9$, wherein $R^9$ represents hydrogen and alkyl radicals;

$R^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone or sulfoxide derivatives thereof;

$R^4$ represents hydrogen and radicals as defined by $R^3$;

$R^7$ and $R^{7'}$, independently represent radicals as defined for $R^3$; amino acid side chains selected from the group consisting of valine, isoleucine, glycine, alanine, allo-isoleucine, asparagine, leucine, glutamine, and t-butylglycine; radicals represented by the formulas $-C(O)R^{16}$, $-CO_2R^{16}$, $-SO_2R^{16}$, $-SR^{16}$, $-CONR^{16}R^{17}$, $-CF_3$ and $-NR^{16}R^{17}$; or $R^7$ and $R^{7'}$ together with the carbon atom to which they are attached form a cycloalkyl radical;

$R^8$ represents cyano, hydroxyl, alkyl, alkoxy, cycloalkyl, aryl, aralkyl, heterocycloalkyl and heteroaryl radicals and radicals represented by the formulas $C(O)R^{16}$, $CO_2R^{16}$, $SO_2R^{16}$, $SR^{16}$, $CONR^{16}R^{17}$, $CF_3$ and $NR^{16}R^{17}$;

wherein $R^{16}$ and $R^{17}$ independently represent hydrogen and radicals as defined for $R^3$, or $R^{16}$ and $R^{17}$ together with a nitrogen to which they are attached in the formula $NR^{16}R^{17}$ represent heterocycloalkyl and heteroaryl radicals;

n represents an integer of from 0 to 6;

A more preferred family of compounds within Formula II consists of compounds wherein:

R represents hydrogen, alkyl, alkenyl, cycloalkyl, aryl, aralkyl, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents $CH_2C(O)NHCH_3$, $C(CH_3)_2(SCH_3)$, $C(CH_3)_2(S[O]CH_3)$, $C(CH_3)_2(S[O]_2CH_3)$, alkyl, alkenyl and alkynyl radicals, and amino acid side chains selected from the group consisting of asparagine, valine, threonine, allo-threonine, isoleucine, tert-leucine, S-methyl cysteine and methionine and the sulfone and sulfoxide derivatives thereof, alanine, and allo-isoleucine;

$R^2$ represents alkyl, cycloalkylalkyl and aralkyl radicals, which radicals are optionally substituted with halogen radicals and radicals represented by the formula $-OR^9$ and $-SR^9$ wherein $R^9$ represents alkyl radicals; and $R^3$ represents alkyl, haloalkyl, alkenyl, alkoxyalkyl, cycloalkyl, cycloalkylalkyl, heterocycloalkyl, heterocycloalkylalkyl, aryl, aralkyl and heteroaralkyl radicals;

$R^4$ represents hydrogen, alkyl, cycloalkyl, cycloalkylalkyl, aryl, heteroaryl, aralkyl, heteroaralkyl, heterocycloalkyl and heterocycloalkylalkyl radicals;

$R^7$ and $R^{7'}$ independently represent alkyl and aralkyl radicals or together with the carbon atom to which they are attached form a cycloalkyl radical having from 3 to 8 carbon atoms;

$R^8$ represents alkylcarbonyl, aryl, aroyl, aryloxy, aralkanoyl, cyano, hydroxycarbonyl, arylsulfonyl, alkylsulfonyl, alkylthio, hydroxyl, alkoxy, heteroaryl, dialkylaminocarbonyl, dialkylamino, cycloalkylamino, heterocyclylamino and alkoxycarbonyl radicals; and n is an integer of from 0 to 6;

Of highest interest are compounds within Formula II wherein

R represents alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

R¹ represents CH₂C(O)NHCH₃, C(CH₃)₂(SCH₃), C(CH₃)₂(S[O]CH₃), C(CH₃)₂(S[O]₂CH₃), methyl, propargyl, t-butyl, isopropyl and sec-butyl radicals, and amino acid side chains selected from the group consisting of asparagine, valine, S-methyl cysteine, allo-iso-leucine, iso-leucine, and beta-cyano alanine side chains;

R² represents CH₃SCH₂CH₂—, iso-butyl, n-butyl, benzyl, 4-fluorobenzyl, 2-naphthylmethyl and cyclohexylmethyl radicals;

R³ represents propyl, isoamyl, n-butyl, isobutyl, cyclohexyl, cyclohexylmethyl, benzyl and pyridylmethyl radicals;

R⁴ represents hydrogen and methyl, ethyl, i-propyl, propyl, n-butyl, t-butyl, 1,1-dimethylpropyl, cyclohexyl and phenyl radicals;

R⁷ and R⁷' independently represent methyl, ethyl, propyl and butyl radicals, or together with the carbon atom to which they are attached form a cyclopropyl, cyclobutyl, cyclopentyl or cyclohexyl radical;

R⁸ represents methylcarbonyl, phenyl, hydroxy, methoxy, cyano, methoxycarbonyl, ethoxycarbonyl, isopropoxycarbonyl, t-butoxycarbonyl, benzyloxycarbonyl, carboxyl, methoxycarbonyl, methylsulfonyl, methylthio, phenylsulfonyl, phenyl, 2-, 3- or 4-pyridyl, 2-, 3- or 4-pyridyl N-oxide, N,N-dimethylamino, 1-piperidinyl, 4-morpholinyl, 4-(N-methyl)piperazinyl and 1-pyrrolidinyl.

Another family of compounds of particular interest within Formula I are compounds embraced by Formula III:

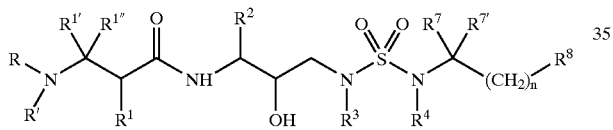

(III)

wherein:
R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, alkyl, alkenyl, cycloalkyl, aryl, aralkyl, aryloxyalkyl, alkoxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for R³ or R and R' together with the nitrogen to which they are attached represent heterocycloalkyl and heteroaryl radical;

R¹ represents hydrogen, —CH₂SO₂NH₂, —CH₂CO₂CH₃, —CO₂CH₃, —CONH₂, —CH₂C(O) NHCH₃, —C(CH₃)₂(SH), —C(CH₃)₂(SCH₃), —C(CH₃)₂(S[O]CH₃), —C(CH₃)₂(S[O]₂CH₃), alkyl, haloalkyl, alkenyl, alkynyl and cycloalkyl radicals, and amino acid side chains selected from asparagine, S-methyl cysteine and the sulfoxide (SO) and sulfone (SO₂) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

R¹' and R¹'' independently represent hydrogen and radicals as defined for R¹ or one of R¹' and R¹'', together with R¹ and the carbon atoms to which R¹, R¹' and R¹'' are attached, represent a cycloalkyl radical;

R² represents alkyl, aryl, cycloalkyl, cycloalkylalkyl and aralkyl radicals, which radicals are optionally substituted with a group selected from alkyl and halogen radials, —NO₂, —C≡N, CF₃, —OR⁹ and —SR⁹, wherein R⁹ represents hydrogen and alkyl radicals;

R³ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone or sulfoxide derivatives thereof;

R⁴ represents hydrogen and radicals as defined by R³;

R⁷ and R⁷' independently represent radicals as defined for R³; amino acid side chains selected from the group consisting of valine, isoleucine, glycine, alanine, allo-isoleucine, leucine, asparagine, glutamine, and t-butylglycine; radicals represented by the formulas —C(O)R¹⁶, —CO₂R¹⁶, —SO₂R¹⁶, —SR¹⁶, —CONR¹⁶R¹⁷, —CF₃ and —NR¹⁶R¹⁷; or R⁷ and R⁷' together with the carbon atom to which they are attached form a cycloalkyl radical;

R⁸ represents cyano, hydroxyl, alkyl, alkoxy, cycloalkyl, aryl, aralkyl, heterocycloalkyl and heteroaryl radicals and radicals represented by the formulas C(O)R¹⁶, CO₂R¹⁶, SO₂R₁₆, SR¹⁶, CONR¹⁶R¹⁷, CF₃ and NR¹⁶R¹⁷;

wherein R¹⁶ and R¹⁷ independently represent hydrogen and radicals as defined for R³, or R¹⁶ and R¹⁷ together with a nitrogen to which they are attached in the formula NR¹⁶R¹⁷ represent heterocycloalkyl and heteroaryl radicals;

n represents an integer of from 0 to 6;

A more preferred family of compounds within Formula III consists of compounds wherein R represents an arylalkanoyl, heteroaroyl, aryloxyalkanoyl, aryloxycarbonyl, alkanoyl, aminocarbonyl, mono-substituted aminoalkanoyl, or disubstituted aminoalkanoyl, or mono-or dialkylaminocarbonyl radical;

R' represents hydrogen and radicals as defined for R³ or R and R' together with the nitrogen to which they are attached represent a heterocycloalkyl or heteroaryl radical;

$R^1$, $R^{1'}$ and $R^{1''}$ independently represent hydrogen and alkyl radicals having from 1 to about 4 carbon atoms, alkenyl, alkynyl, aralkyl radicals, and radicals represented by the formula —$CH_2C(O)R''$ or —$C(O)R''$ wherein $R''$ represents $R^{38}$, —$NR^{38}R^{39}$ and $OR^{38}$ wherein $R^{38}$ and $R^{39}$ independently represent hydrogen and alkyl radicals having from 1 to about 4 carbon atoms;

$R^2$ represents alkyl, cycloalkylalkyl and aralkyl radicals, which radicals are optionally substituted with halogen radicals and radicals represented by the formula —$OR^9$ and —$SR^9$ wherein $R^9$ represents hydrogen and alkyl radicals; and $R^3$ represents alkyl, haloalkyl, alkenyl, alkynyl, alkoxyalkyl, cycloalkyl, cycloalkylalkyl, heterocycloalkyl, heterocycloalkylalkyl, aryl, aralkyl, heteroaryl and heteroaralkyl radicals;

$R^4$ represents hydrogen, alkyl, cycloalkyl, cycloalkylalkyl, aryl, heteroaryl, aralkyl, heteroaralkyl, heterocycloalkyl and heterocycloalkylalkyl radicals;

$R^7$ and $R^{7'}$ independently represent alkyl and aralkyl radicals or together with the carbon atom to which they are attached form a cycloalkyl radical having from 3 to 8 carbon atoms;

$R^8$ represents alkylcarbonyl, aryl, aroyl, aryloxy, aralkanoyl, cyano, hydroxycarbonyl, arylsulfonyl, alkylsulfonyl, alkylthio, hydroxyl, alkoxy, heteroaryl, dialkylaminocarbonyl, dialkylamino, cycloalkylamino, heterocyclylamino and alkoxycarbonyl radicals.

Of highest interest are compounds of Formula III wherein:

R represents an arylalkanoyl, aryloxycarbonyl, heteroaroyl, aryloxyalkanoyl, alkanoyl, aminocarbonyl, mono-substituted aminoalkanoyl, or disubstituted aminoalkanoyl, or mono-or dialkylaminocarbonyl radical;

R' represents hydrogen and radicals as defined for $R^3$ or R and R' together with the nitrogen to which they are attached represent a heterocycloalkyl or heteroaryl radical;

$R^1$, $R^{1'}$ and $R^{1''}$ independently represent hydrogen, methyl, ethyl, benzyl, phenylpropyl, —$C(O)NH_2$ and propargyl radicals;

$R^2$ represents $CH_3SCH_2CH_2$—, iso-butyl, n-butyl, benzyl, 4-fluorobenzyl, 2-naphthylmethyl and cyclohexylmethyl radicals;

$R^3$ represents propyl, isobutyl, isoamyl, n-butyl, n-propyl, cyclohexyl, cyclohexylmethyl, benzyland pyridylmethyl radicals;

$R^4$ represents hydrogen and methyl, ethyl, i-propyl, n-butyl, t-butyl, 1,1-dimethylpropyl, cyclohexyl and phenyl radicals;

$R^7$ and $R^{7'}$ independently represent methyl, ethyl, propyl and butyl radicals, or together with the carbon atom to which they are attached form a cyclopropyl, cyclobutyl, cyclopentyl or cyclohexyl radical;

$R^8$ represents methylcarbonyl, phenyl, hydroxy, methoxy, cyano, methoxycarbonyl, ethoxycarbonyl, isopropoxycarbonyl, t-butoxycarbonyl, benzyloxycarbonyl, carboxyl, methoxycarbonyl, methylsulfonyl, methylthio, phenylsulfonyl, phenyl, 2-, 3- or 4-pyridyl, 2-, 3- or 4-pyridyl N-oxide, N,N-dimethylamino, 1-piperidinyl, 4-morpholinyl, 4-(N-methyl)piperazinyl and 1-pyrrolidinyl.

Another family of compounds of particular interest within Formula I are compounds embraced by Formula IV:

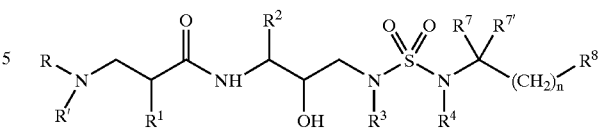

(IV)

wherein:

R represents hydrogen, alkyl, alkenyl, cycloalkyl, aryl, aralkyl, aryloxyalkyl, heteroaryloxyalkyl, hydroxyalkyl, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, alkoxyalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, aminocarbonyl, aminoalkanoyl, and mono- and disubstituted aminocarbonyl and mono- and disubstituted aminoalkanoyl, radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals, and amino acid side chains selected from asparagine, S-methyl cysteine and methionine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

$R^2$ represents alkyl, aryl, cycloalkyl, cycloalkylalkyl and aralkyl radicals, which radicals are optionally substituted with a group selected from alkyl and halogen radicals, —$NO_2$, —$C\equiv N$, $CF_3$, —$OR^9$, —$SR^9$, wherein $R^9$ represents hydrogen and alkyl;

$R^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl and arylthioalkyl radicals and the sulfone or sulfoxide derivatives thereof;

$R^4$ represents hydrogen and radicals as defined for $R^3$;

R⁷ and R⁷' independently represent radicals as defined for R₃; amino acid side chains selected from the group consisting of valine, isoleucine, glycine, alanine, allo-isoleucine, asparagine, leucine, glutamine, and t-butylglycine; radicals represented by the formulas —C(O)R¹⁶, —CO R¹⁶, —SO₂R¹⁶, —SR¹⁶, —CONR¹⁶R¹⁷, —CF₃ and —NR¹⁶R¹⁷; or R⁷ and R⁷' together with the carbon atom to which they are attached form a cycloalkyl radical;

R⁸ represents cyano, hydroxyl, alkyl, alkoxy, cycloalkyl, aryl, aralkyl, heterocycloalkyl and heteroaryl radicals and radicals represented by the formulas C(O)R¹⁶, CO₂R¹⁶, SO₂R¹⁶, SR¹⁶, CONR¹⁶R¹⁷, CF₃ and NR¹⁶R¹⁷;

wherein R¹⁶ and R¹⁷ independently represent hydrogen and radicals as defined for R³, or R¹⁶ and R¹⁷ together with a nitrogen to which they are attached in the formula NR¹⁶R¹⁷ represent heterocycloalkyl and heteroaryl radicals;

n represents an integer of from 0 to 6.

A more preferred family of compounds within Formula IV consists of compounds wherein R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for R³ or R and R' together with the nitrogen to which they are attached represent heterocycloalkyl and heteroaryl radical;

R¹ represents hydrogen, alkyl, alkenyl, and alkynyl radicals, and amino acid side chains selected from the group consisting of asparagine, valine, threonine, allo-threonine, isoleucine, tert-leucine, S-methyl cysteine and the sulfone and sulfoxide derivatives thereof, alanine, and allo-isoleucine;

R² represents alkyl, cycloalkylalkyl and aralkyl radicals, which radicals are optionally substituted with halogen radicals and radicals represented by the formula —OR⁹ and —SR⁹ wherein R⁹ represents hydrogen and alkyl and halogen radicals;

R³ represents alkyl, haloalkyl, alkenyl, alkoxyalkyl, cycloalkyl, cycloalkylalkyl, heterocycloalkyl, heterocycloalkylalkyl, aryl, aralkyl, heteroaryl and heteroaralkyl radicals;

R⁴ represents hydrogen, alkyl, cycloalkyl, cycloalkylalkyl, aryl, heteroaryl, aralkyl, heteroaralkyl, heterocycloalkyl and heterocycloalkylalkyl radicals;

R⁷ and R⁷' independently represent alkyl and aralkyl radicals or together with the carbon atom to which they are attached form a cycloalkyl radical having from 3 to 8 carbon atoms;

R⁸ represents alkylcarbonyl, aryl, aroyl, aryloxy, aralkanoyl, cyano, hydroxycarbonyl, arylsulfonyl, alkylsulfonyl, alkylthio, hydroxyl, alkoxy, heteroaryl, dialkylaminocarbonyl, dialkylamino, cycloalkylamino, heterocyclylamino and alkoxycarbonyl radicals; and n represents an integer of from 0 to 6.

Of highest interest are compounds within Formula IV wherein

R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for R₃ or R and R' together with the nitrogen to which they are attached represent heterocycloalkyl and heteroaryl radical;

R¹ represents hydrogen, methyl, propargyl, t-butyl, iso-propyl and sec-butyl radicals, and amino acid side chains selected from the group consisting of asparagine, valine, S-methyl cysteine, allo-iso-leucine, iso-leucine, threonine, serine, aspartic acid, beta-cyano alanine, and allo-threonine side chains;

R² represents CH₃SCH₂CH₂—, iso-butyl, n-butyl, benzyl, 4-fluorobenzyl, 2-naphthylmethyl and cyclohexylmethyl radicals;

R³ represents propyl, isobutyl, isoamyl, n-butyl, cyclohexyl, cyclohexylmethyl, benzyl and pyridylmethyl radicals;

R⁴ represents hydrogen and methyl, ethyl, i-propyl, n-propyl, n-butyl, t-butyl, 1,1-dimethylpropyl, cyclohexyl and phenyl radicals;

R⁷ and R⁷' independently represent methyl, ethyl, propyl and butyl radicals, or together with the carbon atom to which they are attached form a cyclopropyl, cyclobutyl, cyclopentyl or cyclohexyl radical;

R⁸ represents methylcarbonyl, phenyl, hydroxy, methoxy, cyano, methoxycarbonyl, ethoxycarbonyl, isopropoxycarbonyl, t-butoxycarbonyl, benzyloxycarbonyl, carboxyl, methoxycarbonyl, methylsulfonyl, methylthio, phenylsulfonyl, phenyl, 2-, 3- or 4-pyridyl, 2-, 3- or 4-pyridyl N-oxide, N,N-dimethylamino, 1-piperidinyl, 4-morpholinyl, 4-(N-methyl)piperazinyl and 1-pyrrolidinyl; and n represents an integer of from 0 to 6.

As utilized herein, the term "alkyl", alone or in combination, means a straight-chain or branched-chain alkyl-radical containing from 1 to about 10, preferably from 1 to 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radical having one or more double bonds and containing from 2 to about 18 carbon atoms preferably from 2 to 8 carbon atoms. Examples of suitable alkenyl radicals include ethenyl, propenyl; 1,4-butadienyl, 12-octadecene and the like. The term "alkynyl", alone or in combination, means a straight-chain hydrocarbon radical having one or more triple bonds and containing from 2 to about 10 carbon atoms, preferably from 2 to 8 carbon atoms. Examples of alkynyl radicals include ethynyl, propynyl, (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains from about 3 to about 8 carbon atoms and is cyclic. The term "cycloalkylalkyl" means an alkyl radical as defined above which is substituted by a cycloalkyl radical containing from about 3 to about 8, preferably from 3 to 6 carbon atoms. Examples of such cycloalkyl radicals include cyclopropyl, cyclobutyl, cyclopentyl, cyclohexyl and the like. The term "aryl", alone or in combination, means a phenyl or naphthyl radical which optionally carries one or more substituents selected from alkyl, alkoxy, halogen, hydroxy, amino, nitro, cyano, haloalkyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula —C(O)—O-aralkyl in which the term "aralkyl" has the significance given above. An example of an aralkoxycarbonyl radical is benzyloxycarbonyl. The term "aryloxy" means a radical of the formula aryl-O—in which the term aryl has the significance given above. The term "alkanoyl", alone or in combination, means an acyl radical derived from an alkanecarboxylic acid wherein alkane means a radical as defined above for alkyl. Examples of alkanoyl radicals include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl,2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl,4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclyalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e.=N—) by oxido and which is attached via a carbon atom. The heteroaryl portion of a heteroaroyl, heteroaryloxycarbonyl, or a heteroaralkoxy carbonyl group or the like is an aromatic monocyclic, bicyclic, or tricyclic heterocycle which contains the hetero atoms and is optionally substituted as defined above with respect to the definition of heterocyclyl. Such heterocyclyl and heteroaryl radicals have from four to about 12 ring members, preferably from 4 to 10 ring members. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-,2-,4- or 5-benzimidazolyl, and the like. The term "cycloalkylalkoxycarbonyl" means an acyl group derived from a cycloalkylalkoxycarboxylic acid of the formula cycloalkylalkyl-O—COOH wherein cycloalkylalkyl has the significance given above. The term "aryloxyalkanoyl" means an acyl radical of the formula aryl-O-alkanoyl wherein aryl and alkanoyl have the significance given above. The term "heterocyclyloxycarbonyl" means an acyl group derived from heterocyclyl-O—COOH wherein heterocyclyl is as defined above. The term "heterocyclylalkanoyl" is an acyl radical derived from a heterocyclyl-substituted alkane carboxylic acid wherein heterocyclyl has the significance given above. The term "heterocyclylalkoxycarbonyl" means an acyl radical derived from a heterocyclyl-substituted alkane-O—COOH wherein heterocyclyl has the significance given above. The term "heteroaryloxycarbonyl" means an acyl radical derived from a carboxylic acid represented by heteroaryl-O—COOH wherein heteroaryl has the significance given above. The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl" means an acyl group derived from an amino-substituted alkanecarboxylic acid wherein the amino group can be a primary, secondary or tertiary amino group containing substituents selected from hydrogen, and alkyl, aryl, aralkyl, cycloalkyl, cycloalkylalkyl radicals and the like. The term "halogen" means fluorine, chlorine, bromine or iodine. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R), which is the preferred stereochemistry for the compounds of the present invention. However, such procedures are generally applicable to those compounds of opposite configuration, e.g., where the stereochemistry about the hydroxyl group is (S). In addition, the compounds having the (R) stereochemistry can be utilized to produce those having the (S) stereochemistry. For example, a compound having the (R) stereochemistry can be inverted to the (S) stereochemistry using well-known methods.

Preparation of Compounds of Formula I

The compounds of the present invention represented by Formula I above can be prepared utilizing the following general procedure. This procedure is schematically shown in the following Schemes I–V:

SCHEME I

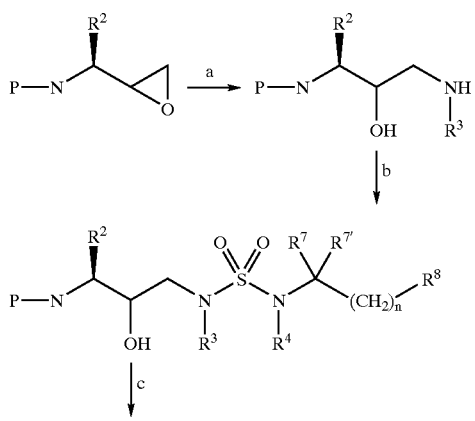

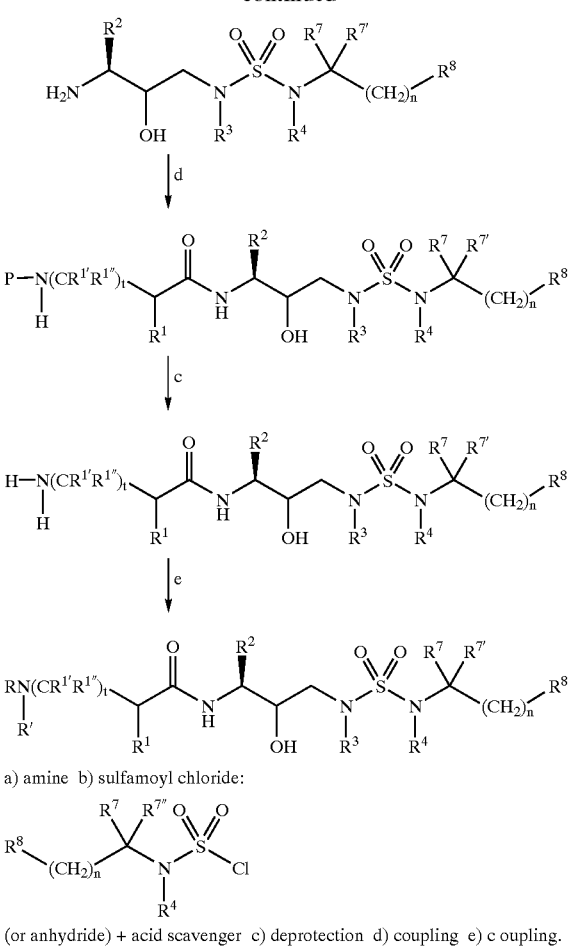

a) amine b) sulfamoyl chloride:

(or anhydride) + acid scavenger c) deprotection d) coupling e) coupling.

SCHEME II

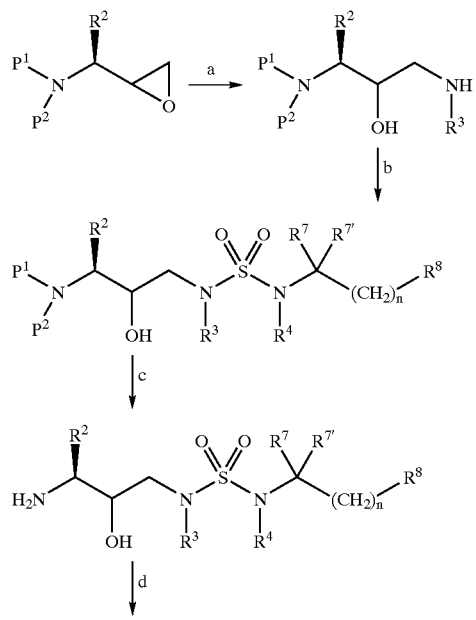

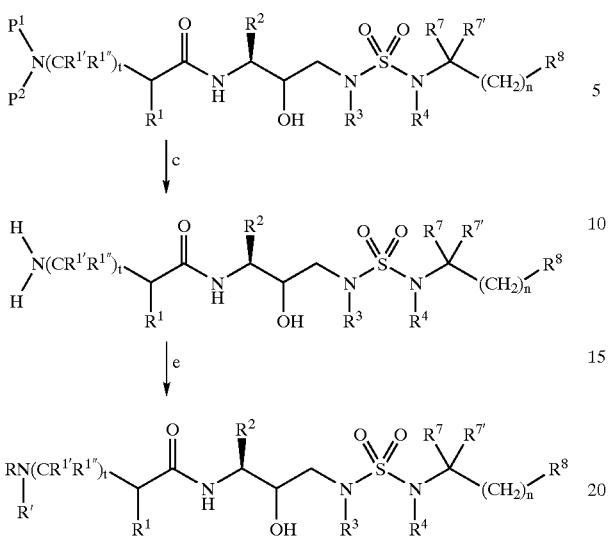
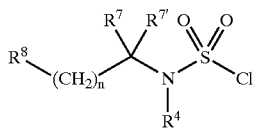

a) amine b) sulfamoyl chloride:

(or anhydride) + acid scavenger c) deprotection d) coupling e) coupling.

SCHEME III

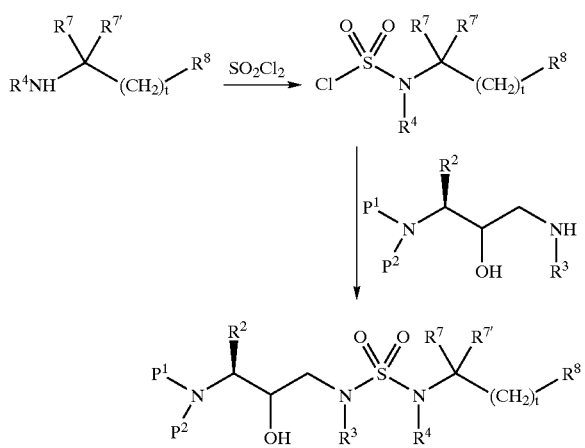

SCHEME IV

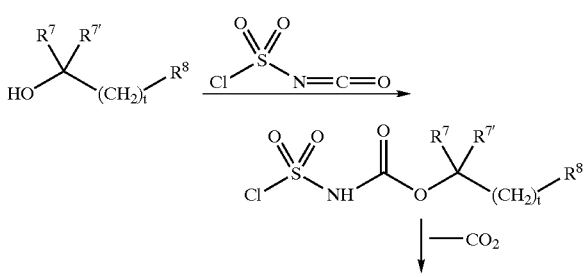

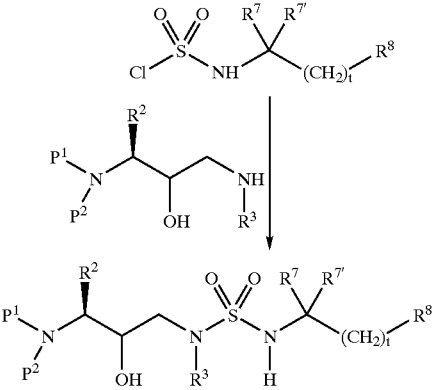

An N-protected chloroketone derivative of an amino acid having the formula:

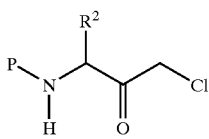

wherein P represents an amino protecting group, and $R^2$ is as defined above, is reduced to the corresponding alcohol utilizing an appropriate reducing agent. Suitable amino protecting groups are well known in the art and include carbobenzoxy, t-butoxycarbonyl, and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, tetrahydrofuran, and the like. The N-protected chloroketones are commercially available, e.g., such as from Bachem, Inc., Torrance, Calif. Alternatively, the chloroketones can be prepared by the procedure set forth in S. J. Fittkau, *J. Prakt. Chem.*, 315, 1037 (1973), and subsequently N-protected utilizing procedures which are well known in the art.

The halo alcohol can be utilized directly, as described below, or, preferably, is then reacted, preferably at room temperature, with a suitable base in a suitable solvent system to produce an N-protected amino epoxide of the formula:

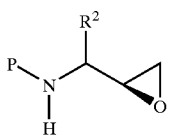

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared starting with an L-amino acid which is reacted with a suitable amino-protecting group in a suitable solvent to produce an amino-protected L-amino acid ester of the formula:

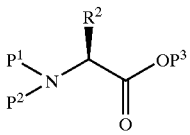

wherein $P^1$ and $P^2$ independently represent hydrogen, benzyl and amino-protecting groups (as defined above), provided that $P^1$ and $P^2$ are not both hydrogen; $P^3$ represents carboxyl-protecting group, e.g., methyl, ethyl, benzyl, tertiary-butyl and the like; and $R^2$ is as defined above.

The amino-protected L-amino acid ester is then reduced, to the corresponding alcohol. For example, the amino-protected L-amino acid ester can be reduced with diisobutylaluminum hydride at −78° C. in a suitable solvent such as toluene. The resulting alcohol is then converted, for example, by way of a Swern oxidation, to the corresponding aldehyde of the formula:

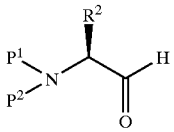

wherein $P^1$, $P^2$ and $R^2$ are as defined above. Thus, a dichloromethane solution of the alcohol is added to a cooled (−75 to −68° C.) solution of oxalyl chloride in dichloromethane and DMSO in dichloromethane and stirred for 35 minutes.

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

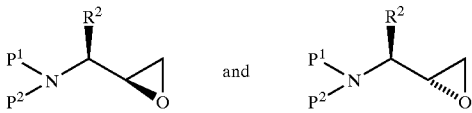

The diastereomers can be separated e.g., by chromatography, or, alternatively, once reacted in subsequent steps the diastereomeric products can be separated. For compounds having the (S) stereochemistry, a D-amino acid can be utilized in place of the L-amino acid.

The amino epoxide is then reacted, in a suitable solvent system, with an equal amount, or preferably an excess of, a desired amine of the formula:

$R^3NH_2$ wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic organic solvents such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. The resulting product is a 3-(N-protected amino)-3-($R^2$)-1-(NHR$^3$)-propan-2-ol derivative (hereinafter referred to as an amino alcohol) can be represented by the formulas:

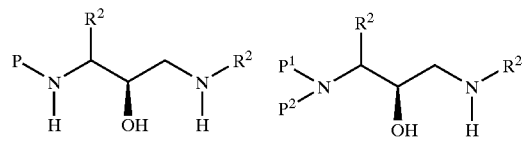

wherein P, $P^1$, $P^2$, $R^2$ and $R^3$ are as described above. Alternatively, a haloalcohol can be utilized in place of the amino epoxide.

The amino alcohol defined above is then reacted in a suitable solvent with a sulfamoyl halide, e.g. sulfamoyl chloride $[R^8(CH_2)_nC(R^7R^{7'})][R^4]NSO_2Cl$ or sulfamoyl anhydride in the presence of an acid scavenger. Suitable solvents in which the reaction can be conducted include methylene chloride, tetrahydrofuran. Suitable acid scavengers include triethylamine, pyridine. The resulting sulfamic acid derivative can be represented, depending on the epoxide utilized, by the formulas;

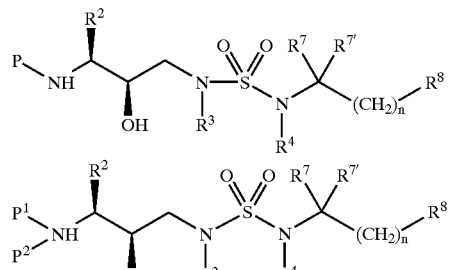

wherein P, $P^1$, $P^2$, $R^2$, $R^3$, $R^4$, $R^5$, $R^7$, $R^{7'}$, $R^8$ and n are as defined above. These intermediates are useful for preparing inhibitor compounds of the present invention and are also active inhibitors of retroviral proteases.

The sulfamoyl halides of the formula $[R^8(CH_2)_nC(R^7R^{7'})][R^4]NSO_2X$, wherein $R^4$ is hydrogen can be prepared by the reaction of a suitable isocyanate of the formula $[R^8(CH_2)_nC(R^7R^{7'})][R^4]NCO$ with fuming sulfuric acid to produce the corresponding sulfamate which is then converted to the halide by well known procedures, such as by treating the sulfamate with $PCl_5$. Alternatively the isocyanate can be treated with chlorosulfonic acid to produce the corresponding sulfamoyl chloride directly.

The sulfamoyl halides of the formula $[R^8(CH_2)_nC(R^7R^{7'})][R^4]NSO_2Cl$, wherein $R^4$ is other than hydrogen, can be prepared by reacting an amine of the formula $[R^8(CH_2)_nC(R^7R^{7'})][R^4]NH$, preferably as a salt such as the hydrochloride, with sulfuryl chloride in a suitable solvent such as acetonitrile. The reaction mixture is gradually warmed to reflux temperature and maintained at the reflux temperature until the reaction is complete. Alternatively, sulfamoyl halides of the formula $[R^8(CH_2)_nC(R^7R^{7'})][R^4]$ NSO$_2$Cl can be prepared by reacting an amine of the formula [R$^8$(CH$_2$)$_n$C(R$^7$R$^{7'}$)][R$^4$]NH with sulfuryl chloride in boiling MeCN as disclosed in Matier et al., *J. Med. Chem.*, 15, No. 5, p.538 (1972).

Alternatively, the sulfamoyl halide can be prepared by reacting a sulfamoyl halide derivative of an isocyanate, i.e., a derivative of the formula ClSO$_2$NCO with an appropriate alcohol of the formula HOC(R$^7$R$^{7'}$)(CH$_2$)$_n$R$^8$ to produce the corresponding compound of the formula ClSO$_2$NHC(O)OC(R$^7$R$^{7'}$)(CH$_2$)$_n$R$^8$. Following deletion of the carbonyl moiety a sulfamoyl halide of the formula ClSO$_2$NHC(R$^7$R$^{7'}$)(CH$_2$)$_n$R$^8$ is produced. This procedure is described in *J. Org. Chem.*, 54, 5826–5828 (1989). Alternatively, the amino alcohol can be reacted with a chlorosulfonyl methyl ester of the formula ClSO$_2$O alkyl to produce the corresponding derivative and then reacted with an amine of the formula HNR$^4$R$^5$.

Following preparation of the sulfonyl urea derivative, the amino protecting group P or P$^1$ and P$^2$ amino protecting groups are removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Following neutralization of the salt, the amine is then reacted with an amino acid or corresponding derivative thereof represented by the formula (PN[CR$^{1'}$ R$^{1''}$]$_t$ CH(R$^1$)COOH) wherein t, R$^1$, R$^{1'}$ and R$^{1''}$ are as defined above, to produce the antiviral compounds of the present invention having the formula:

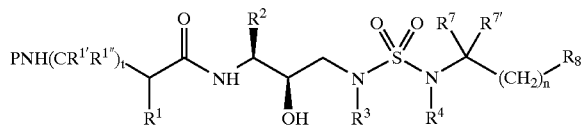

wherein t, P, R$^1$, R$^{1'}$, R$^{1''}$, R$^2$, R$^3$, R$^4$, R$^5$, R$^7$, R$^{7'}$, R$^8$ and n are as defined above. Preferred protecting groups in this instance are a benzyloxycarbonyl group or a t-butoxycarbonyl group. Where the amine is reacted with a derivative of an amino acid, e.g., when t=1 and R$^{1'}$ and R$^{1''}$ are both H, so that the amino acid is a β-amino acid, such β-amino acids can be prepared according to the procedure set forth in a copending application, U.S. Ser. No. 07/345,808. Where t is 1, one of R$^{1'}$ and R$^{1''}$ is H and R$^1$ is hydrogen, so that the amino acid is a homo-β-amino acid, such homo-β-amino acids can be prepared by the procedure set forth in a copending application, U.S. Ser. No. 07/853,561. Where t is 0 and R$^1$ is alkyl, alkenyl, alkynyl, cycloalkyl, —CH$_2$SO$_2$NH$_2$, —CH$_2$CO$_2$CH$_3$, —CO$_2$CH$_3$, —CONH$_2$, —CH$_2$C(O)NHCH$_3$, —C(CH$_3$)$_2$(SH), —C(CH$_3$)$_2$(SCH$_3$), —C(CH$_3$)$_2$[S(O)CH$_3$], —C(CH$_3$)$_2$[S(O$_2$)CH$_3$], or an amino acid side chain, such materials are well known and many are commercially available from Sigma-Aldridh.

The N-protecting group can be subsequently removed, if desired, utilizing the procedures described above, and then reacted with a carboxylate represented by the formula:

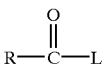

wherein R is as defined above and L is an appropriate leaving group such as a halide. Preferably, where R$^1$ is a side chain of a naturally occurring α-amino acid, R is a 2-quinoline carbonyl group derived from N-hydroxysuccinimide-2-quinoline carboxylate, i.e., L is hydroxy succinimide. A solution of the free amine (or amine acetate salt) and about 1.0 equivalent of the carboxylate are mixed in an appropriate solvent system and optionally treated with up to five equivalents of a base such as, for example, N-methylmorpholine, at about room temperature. Appropriate solvent systems include tetrahydrofuran, methylene chloride or N,N-dimethylformamide, and the like, including mixtures thereof.

Alternatively, the protected amino alcohol from the epoxide opening can be further protected at the newly introduced amino group with a protecting group P' which is not removed when the first protecting P is removed. One skilled in the art can choose appropriate combinations of P and P'. One suitable choice is when P is Cbz and P' is Boc. The resulting compound represented by the formula:

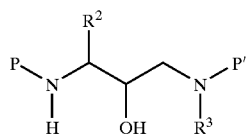

can be carried through the remainder of the synthesis to provide a compound of the formula:

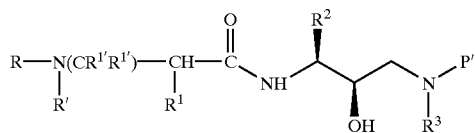

and the new protecting group P' is selectively removed, and following deprotection, the resulting amine reacted to form the sulfamic acid derivative as described above. This selective deprotection and conversion to the sulfonyl urea derivative can be accomplished at either the end of the synthesis or at any appropriate intermediate step if desired.

It is contemplated that for preparing compounds of the Formulas having R$^6$, the compounds can be prepared following the procedure set forth above and, prior to coupling the sulfonamide derivative or analog thereof, e.g. coupling to the amino acid PNH(CH$_2$)$_t$CH(R$^1$)COOH, carried through a procedure referred to in the art as reductive amination. Thus, a sodium cyanoborohydride and an appropriate aldehyde or ketone can be reacted with the sulfonamide derivative compound or appropriate analog at room temperature in order to reductively aminate any of the compounds of Formulas I–IV. It is also contemplated that where R$^3$ of the amino alcohol intermediate is hydrogen, the inhibitor compounds of the present invention wherein R$^3$ is alkyl, or other substituents wherein the α-C contains at least one hydrogen, can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties, such as tautomers thereof as well as compounds, wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall. activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples 1 through 9 illustrate preparation of intermediates. These intermediates are useful in preparing the inhibitor compounds of the present invention as illustrated in Examples 13–17. In addition, the intermediates of Examples 4–9 are also retroviral protease inhibitors and inhibit, in particular, HIV protease.

EXAMPLE 1

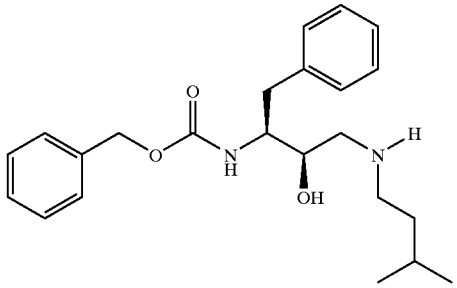

Preparation of N[3(S)-benzyloxycarbonylamino-2(R)-hydroxy-4-phenylbutyl]-N-isoamylamine Part A To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150–151° C. and M+Li$^+$=340.

Part B

To a solution of 6.52 g (0.116 mol, 1.2 equiv.) of potassium hydroxide in 968 mL of absolute ethanol at room temperature, was added 32.3g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1, 2(S)-epoxy-4-phenylbutane, mp 102–103° C. and MH$^+$298.

Part C

A solution of N-benzyloxycarbonyl 3(S)-amino-1,2-(S)-epoxy-4-phenylbutane (1.00 g, 3.36 mmol) and isoamylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3(S)-phenylmethylcarbamoyl)amino-2(R)-hydroxy-4-phenylbutyl]N-[(3-methylbutyl)]amine mp 108.0–109.5° C., MH$^+$ m/z 371.

EXAMPLE 2

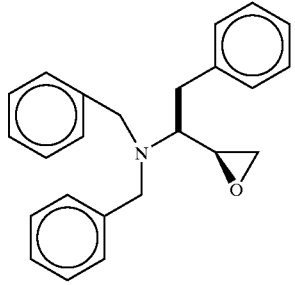

Preparation of N,N-dibenzyl-3(S)-amino-1,2-(S)-epoxy-4-phenylbutane

Step A

A solution of L-phenylalanine (50.0 g, 0.302 mol), sodium hydroxide (24.2 g, 0.605 mol) and potassium carbonate (83.6 g, 0.605 mol) in water (500 ml) is heated to 97° C. Benzyl bromide (108.5 ml, 0.912 mol) is then slowly added (addition time ~25 min). The mixture is then stirred at 97° C. for 30 minutes. The solution is cooled to room temperature and extracted with toluene (2×250 ml). The combined organic layers are then washed with water, brine, dried over magnesium sulfate, filtered and concentrated to give an oil product. The crude product is then used in the next step without purification.

Step B

The crude benzylated product of the above step is dissolved in toluene (750 ml) and cooled to −55° C. A 1.5 M solution of DIBAL-H in toluene (443.9 ml, 0.666 mol) is then added at a rate to maintain the temperature between −55° to −50° C. (addition time ~1 hour). The mixture is stirred for 20 minutes at −55° C. The reaction is quenched at −55° C. by the slow addition of methanol (37 ml). The cold solution is then poured into cold (5° C.) 1.5 N HCl solution (1.8 L). The precipitated solid (approx. 138 g) is filtered off and washed with toluene. The solid material is suspended in a mixture of toluene (400 ml) and water (100 ml). The mixture is cooled to 5° C., treated with 2.5 N NaOH (186 ml) and then stirred at room temperature until the solid is dissolved. The toluene layer is separated from the aqueous phase and washed with water and brine, dried over magnesium sulfate, filtered and concentrated to a volume of 75 ml (89 g). Ethyl acetate (25 ml) and hexane (25 ml) are then added to the residue upon which the alcohol product begins to crystallize. After 30 min., an additional 50 ml hexane is added to promote further crystallization. The solid is filtered off and washed with 50 ml hexane to give approximately 35 g of material. A second crop of matrial can be isolated by refiltering the mother liquor. The solids are combined and recrystallized from ethyl acetate (20 ml) and hexane (30 ml) to give, in 2 crops, approximately 40 g (40% from L-phenylalanine) of analytically pure alcohol product. The mother liquors are combined and concentrated (34 g). The residue is treated with ethyl acetate and hexane which provides an additional 7 g (~7% yield) of slightly impure solid product. Further optimization in the recovery from the mother liquor is probable.

Step C

A solution of oxalyl chloride (8.4 ml, 0.096 mol) in dichloromethane (240 ml) is cooled to −74° C. A solution of DMSO (12.0 ml, 0.155 mol) in dichloromethane (50 ml) is then slowly added at a rate to maintain the temperature at −74° C. (addition time ~1.25 hr). The mixture is stirred for 5 min.. followed by addition of a solution of the alcohol (0.074 mol) in 100 ml of dichloromethane (addition time ~20 min., temp. −75° C. to −68° C.). The solution is stirred at −78° C. for 35 minutes. Triethylamine (41.2 ml, 0.295 mol) is then added over 10 min. (temp. −78° to −68° C.) upon which the ammonium salt precipitated. The cold mixture is stirred for 30 min. and then water (225 ml) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde was carried on to the next step without purification.

Temperatures higher than −70° C. have been reported in the literature for the Swern oxidation. Other Swern modifications and alternatives to the Swern oxidations are also possible.

A solution of the crude aldehyde 0.074 mol and chloroiodomethane (7.0 ml, 0.096 mol) in, tetrahydrofuran (285 ml) is cooled to −78° C. A 1.6 M solution of n-butyllithium in hexane (25 ml, 0.040 mol) is then added at a rate to maintain the temperature at −75° C. (addition time ~15 min.). After the first addition, additional chloroiodomethane (1.6 ml, 0.022 mol) is added again, followed by n-butyllithium (23 ml, 0.037 mol), keeping the temperature at −75° C. The mixture is stirred for 15 min. Each of the reagents, chloroiodomethane (0.70 ml, 0.010 mol) and n-butyllithium (5 ml, 0.008 mol) are added 4 more times over 45 min. at −75° C. The cooling bath is then removed and the solution warmed to 22° C. over 1.5 hr. The mixture is poured into 300 ml of saturated aq. ammonium chloride solution. The tetrahydrofuran layer is separated. The aqueous phase is extracted with ethyl acetate, (1×300 ml). The combined organic layers are washed with brine, dried over magnesium sulfate, filtered and concentrated to give a brown oil (27.4 g). The product could be used in the next step without purification. The desired diastereomer can be purified by recrystallization at a subsequent step.

Alternately, the product could be purified by chromatography.

EXAMPLE 3

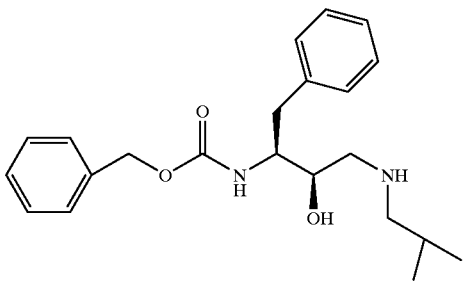

Preparation of N[3(S)-benzyloxycarbonylamino-2 (R)-hydroxy-4-phenyl]N-isobutylamine A solution of N-benzyloxycarbonyl-3(S)-amino-1,2-(S)-epoxy-4-phenyl butane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N[3(S)-benzyloxycarbonylamino-2(R)-hydroxy-4-phenyl] N-isobutylamine, mp 108.0–109.5° C., MH+m/z=371.

EXAMPLE 4

Preparation of Sulfamoyl Chlorides

Method A

An amino acid ester hydrochloride (1 mmol) is suspended in a suitable solvent such as hexane, dichloromethane, toluene and the like, but most preferable acetonitrile. To the well stirred mixture is added sulfuryl chloride (3 mmol) in a suitable solvent, or neat, dropwise over several minutes. The reaction is allowed to stir at zero to reflux temperatures, preferable at reflux, for 1 to 48 hours, preferably for 24 hours. The solvent is removed and the residue triturated with a suitable solvent, such as hexane, pentane, toluene, but most preferably diethyl ether. The solvent is decanted and concentrated. The product may then be utilized as such or purified by distillation or in the case of solids recrystallized from appropriate solvents.

Method B

An alpha-hydroxy ester (1 mmol) is dissolved in an appropriate solvent such as acetonitrile, dichloromethane, toluene and the like, but most preferable hexane. Chlorosulfonyl isocyanate (1 mmol) added neat or in a solvent, preferably in hexane, is added dropwise. The reaction is stirred from zero to reflux, preferably at reflux, for 5 minutes to several hours, preferably for 1 hour. The solvent is then removed and the residue used as such, or taken up in an appropriate solvent, expecially dichloromethane, and filtered to remove any impurities. The product may then be purified by distillation or in the case of solids recrystallized from appropriate solvents.

EXAMPLE 5

Preparation of Sulfamates

An amino alcohol as prepared in Example 3 (1 mmol) and a suitable base, such as triethylamine, pyridine, sodium carbonate, and the like, preferably diisopropylethylamine (1 mmol) are dissolved in a suitable solvent such as ether, chloroform, acetonitrile and the like, but preferably dichloromethane. The sulfamoyl chloride from part A or B of Example 4, neat or dissolved in an appropriate solvent, is added to the above solution. The reaction is stirred at zero to reflux temperatures, but preferably at room temperature for 1 to 48 hours. The product can be purified by silica gel chromatography or by an extractive workup followed by recrystallization.

The following Examples 6–8 illustrate preparation of β-amino acid intermediates. These intermediates can be coupled to the intermediate compounds illustrated by those of Examples 4 and 5 to produce inhibitor compounds of the present invention containing β-amino acids.

EXAMPLE 6

A. Preparation of 4(4-methoxybenzyl)itaconate

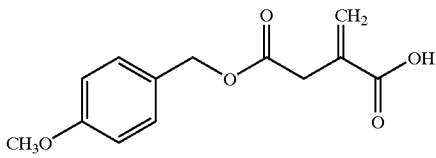

A 5 L three-necked round bottomed flask equipped with constant pressure addition funnel, reflux condenser, nitrogen inlet, and mechanical stirrer was charged with itaconic anhydride (660.8 g, 5.88 mol) and toluene (2300 mL). The solution was warmed to reflux and treated with 4-methoxybenzyl alcohol (812.4 g, 5.88 mol) dropwise over a 2.6 h period. The solution was maintained at reflux for an additional 1.5 h and then the contents were poured into three 2 L erlenmeyer flasks to crystallize. The solution was allowed to cool to room temperature whereupon the desired mono-ester crystallized. The product was isolated by filtration on a Buchner funnel and air dried to give 850.2 g, 58% of material with mp 83–85° C., a second crop, 17% was isolated after cooling of the filtrate in an ice bath. $^1$H NMR (CDCl$_3$) 300 MHz 7.32(d, J=8.7 Hz, 2H), 6.91(d, J=8.7 Hz, 2H), 6.49(s, 1H), 5.85(s, 1H), 5.12(s, 2H), 3.83(s, 3H), 3.40(s, 2H).

B. Preparation of Methyl 4(4-methoxybenzyl)itaconate

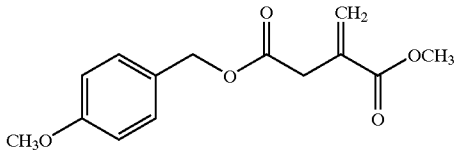

A 5 L three-necked round bottomed flask equipped with reflux condenser, nitrogen inlet, constant pressure addition funnel and mechanical stirrer was charged with 4(4-methoxybenzyl)itaconate (453.4 g, 1.81 mol) and treated with 1,5-diazabicyclo[4.3.0]non-5-ene (275.6 g, 1.81 mol), (DBN), dropwise so that the temperature did not rise above 15° C. To this stirring mixture was added a solution of methyl iodide (256.9 g, 1.81 mol) in 250 mL of toluene from the dropping funnel over a 45 m period. The solution was allowed to warm to room temperature and stirred for an additional 3.25 h.

The precipitated DBN hydroiodide was removed by filtration, washed with toluene and the filtrate poured into a separatory funnel. The solution was washed with sat. aq. NaHCO$_3$ (2×500 mL), 0.2N HCl (1×500 mL), and brine (2×500 mL), dried over anhyd. MgSO$_4$, filtered, and the solvent removed in vacuo. This gave a clear colorless oil, 450.2 g, 94% whose NMR was consistent with the assigned structure. $^1$H NMR (CDCl$_3$) 300 MHz 7.30(d, J=8.7 Hz, 2H), 6.90(d, J=8.7 Hz, 2H), 6.34(s, 1H), 5.71(s, 1H), 5.09(s, 2H), 3.82(s, 3H), 3.73(s, 3H), 3.38(s, 2H). $^{13}$C NMR (CDCl$_3$) 170.46, 166.47, 159.51, 133.55, 129.97, 128.45, 127.72, 113.77, 66.36, 55.12, 51.94, 37.64.

C. Preparation of Methyl 4(4-methoxybenzyl) 2(R)-methylsuccinate

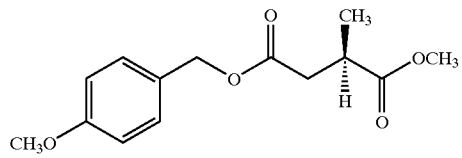

A 500 mL Fisher-Porter bottle was charged with methyl 4(4-methoxybenzyl)itaconate (71.1 g, 0.269 mol), rhodium (R,R) DiPAMP catalyst (204 mg, 0.269 mmol, 0.1 mol %) and degassed methanol (215 mL). The bottle was flushed 5 times with nitrogen and 5 times with hydrogen to a final pressure of 40 psig. The hydrogenation commenced immediately and after ca. 1 h the uptake began to taper off, after 3 h the hydrogen uptake ceased and the bottle was flushed with nitrogen, opened and the contents concentrated on a rotary evaporator to give a brown oil that was taken up in boiling iso-octane (ca. 200 mL, this was repeated twice), filtered through a pad of celite and the filtrate concentrated n vacuo to give 66.6 g, 93% of a clear colorless oil, $^1$H NMR (CDCl$_3$ 300 MHz 7.30(d, J=8.7 Hz, 2H), 6.91(d, J=8.7 Hz, 2H), 5.08(s, 2H), 3.82(s, 3H), 3.67(s, 3H), 2.95(ddq, J=5.7, 7.5, 8.7 Hz, 1H), 2.79(dd, J=8.1, 16.5 Hz, 1H), 2.45(dd, J=5.7, 16.5 Hz, 1H), 1.23(d, J=7.5 Hz, 3H).

D. Preparation of Methyl 2(R)-methylsuccinate

A 3 L three-necked round-bottomed flask equipped with a nitrogen inlet, mechanical stirrer, reflux condenser and constant pressure addition funnel was charged with methyl 4-(4-methoxybenzyl) 2(R)-methylsuccinate (432.6 g, 1.65 mol) and toluene (1200 mL). The stirrer was started and the solution treated with trifluoroacetic acid (600 mL) from the dropping funnel over 0.25 h. The solution turned a deep purple color and the internal temperature rose to 45° C. After stirring for 2.25 h the temperature was 27° C. and the solution had acquired a pink color. The solution was concentrated on a rotary evaporator. The residue was diluted with water (2200 mL) and sat. aq. NaHCO$_3$ (1000 mL). Additional NaHCO$_3$ was added until the acid had been neutralized. The aqueous phase was extrated with ethyl acetate (2×1000 mL) to remove the by-products and the aqueous layer was acidified to pH=1.8 with conc. HCl. This solution was extracted with ethyl acetate (4×2000 mL), washed with brine, dried over anhyd. MgSO$_4$, filtered and concentrated on a rotary evaporator to give a colorless liquid 251 g, >100% that was vacuum distilled through a short path apparatus cut 1: bath temperature 120° C. @>1 mm, bp 25–29° C.; cut 2: bath temperature 140° C. @ 0.5 mm, bp 95–108° C., 151 g, [α]$_d$ @25° C.=+1.38° C.(c=15.475, MeOH), [α]$_{d=+}$8.48° C. (neat); cut 3: bath temperature 140° C., bp 108° C., 36 g, [α]$_d$ @25° C.=+49° C.(c=15.00, MeOH), [α]$_d$ =+8.98° C.(neat). Cuts 2 and 3 were combined to give 189 g, 78% of product, $^1$H NMR (CDCl$_3$) 300 MHz 11.6(brs, 1H), 3.72(s, 3H), 2.92(ddq, J=5.7, 6.9, 8.0 Hz, 1H), 2.81(dd, J=8.0, 16.8 Hz, 1H), 2.47(dd, J=5.7, 16.8 Hz, 1H), 1.26(d, J=6.9 Hz, 3H).

E. Preparation of Methyl Itaconate

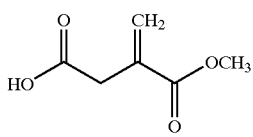

A 50 mL round bottomed flask equipped with reflux condenser, nitrogen inlet and magnetic stir bar was charged with methyl 4(4-methoxybenzyl)itaconate (4.00 g, 16 mmol), 12 mL of toluene and 6 mL of trifluoroacetic acid. The solution was kept at room temperature for 18 hours and then the volatiles were removed in vacuo. The residue was taken up in ethyl acetate and extracted three times with saturated aqueous sodium bicarbonate solution. The combined aqueous extract was acidified to pH=1 with aqueous potassium bisulfate and then extracted three times with ethyl acetate. The combined ethyl acetate solution was washed with saturated aqueous sodium chloride, dried over anhydrous magnesium sulfate, filtered, and concentrated in vacuo. The residue was then vacuum distilled to give 1.23 g, 75% of pure product, bp 85–87 @0.1 mm. $^1$H NMR (CDCl$_3$) 300 MHz 6.34(s, 1H), 5.73(s, 2H), 3.76(s, 3H), 3.38(s, 2H). $^{13}$C NMR (CDCl$_3$) 177.03, 166.65, 129.220, 132.99, 52.27, 37.46.

F. Curtius Rearrangement of Methyl 2(R)-methylsuccinate: Preparation of Methyl N-Moz-α-methyl β-alanine.

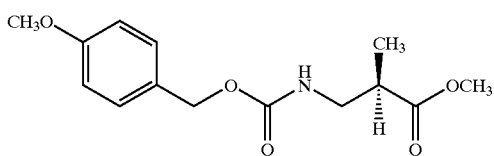

A 5 L four necked round bottomed flask equipped with a nitrogen inlet, reflux condenser, mechanical stirrer, constant pressure addition funnel, and thermometer adapter was charged with methyl 2(R)-methylsuccinate (184.1 g, 1.26 mol), triethylamine (165.6 g, 218 mL, 1.64 mol, 1.3 equivalents), and toluene (1063 mL). The solution was warmed to 85° C. and then treated dropwise with a solution of diphenylphosphoryl azide (346.8 g, 1.26 mol) over a period of 1.2 h. The solution was maintained at that temperature for an additional 1.0 h and then the mixture was treated with 4-methoxybenzyl alcohol (174.1 g, 1.26 mol) over a 0.33 h period from the dropping funnel. The solution was stirred at 88° C. for an additional 2.25 h and then cooled to room temperature. The contents of the flask were poured into a separatory funnel and washed with sat. aq. NaHCO$_3$ (2×500 mL), 0.2N HCl (2×500 mL), brine (1×500 mL), dried over anhyd. MgSO$_4$, filtered, and concentrated in vacuo to give 302.3 g, 85% of the desired product as a slightly brown oil. $_1$H NMR (CDCl$_3$) 300 MHz 7.32(d, J=8.4 Hz, 2H), 6.91(d, J=8.4 Hz, 2H), 5.2(brm, 1H), 5.05(s, 2H), 3.83(s, 3H), 3.70(s, 3H), 3.35(m, 2H), 2.70(m, 2H), 1.20(d, J=7.2 Hz, 3H).

G. Hydrolysis of Methyl N-Moz-α-methyl β-alanine: Preparation of α-methyl β-alanine Hydrochloride

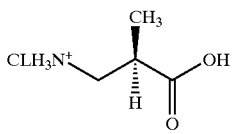

A 5 L three-necked round bottomed flask equipped with a reflux condenser, nitrogen inlet and mechanical stirrer was charged with methyl N-Moz-α-methyl β-alanine (218.6 g, 0.78 mol), glacial acetic acid (975 mL) and 12N hydrochloric acid (19.60 mL). The solution was then heated to reflux for 3h. After the solution had cooled to room temperature (ca. 1h) the aqueous phase was decanted from organic residue (polymer) and the aqueous phase concentrated on a rotary evaporator. Upon addition of acetone to the concentrated residue a slightly yellow solid formed that was slurried with acetone and the white solid was isolated by filtration on a Buchner funnel. The last traces of acetone were removed by evacuation to give 97.7 g, 90% of pure product, mp 128.5–130.5° C. [α]$_d$ @25° C.=9.0° C. (c=2.535, Methanol). $^1$H NMR (D$_2$O) 300 MHz 3.29(dd, J=8.6, 13.0 Hz, 1H), 3.16(dd, J=5.0, 13.0m Hz, 1H), 2.94 (ddq, J=7.2, 5.0, 8.6 Hz, 1H), 1.30(d,J=7.2 Hz, 3H); $^{13}$C NMR (D$_2$O) 180.84, 44.56, 40.27, 17.49.

H. Preparation of N-Boc α-Methyl β-Alanine

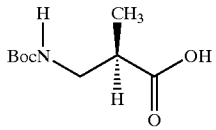

A solution of a-methyl b-alanine hydrochloride (97.7 g, 0.70 mol) in water (1050 mL) and dioxane (1050 mL) the pH was adjusted to 8.9 with 2.9N NaOH solution. This stirring solution was then treated with di-tert- butyl pyrocarbonate (183.3 g, 0.84 mol, 1.2 equivalents) all at once. The pH of the solution was maintained between 8.7 and 9.0 by the periodic addition of 2.5N NaOH solution. After 2.5 h the pH had stabilized and the reaction was judged to be complete. The solution was concentrated on a rotary evaporator (the temperature was maintained at <40° C.). The excess di-tert -butyl pyrocarbonate was removed by extraction with dichloromethane and then the aqueous solution was acidified with cold 1N HCl and immediately extracted with ethyl acetate (4×1000 mL). The combined ethyl acetate extract was washed with brine, dried over anhyd. MgSO$_4$, filtered and concentrated on a rotary evaporator to give a thick oil 127.3 g, 90% crude yield that was stirred with n-hexane whereupon crystals of pure product formed, 95.65 g, 67%, mp 76–78° C., [α]$_d$ @25° C.=−11.8° C. (c=2.4, EtOH). A second crop was obtained by concentration of the filtrate and dilution with hexane, 15.4 g, for a combined yield of 111.05 g, 78%. $^1$H NMR (acetone D$_6$) 300 MHz 11.7 (brs, 1H), 6.05 (brs 1H), 3.35 (m, 1H), 3.22 (m, 1H), 2.50 (m, 1H), 1.45(s, 9H), 1.19 (d, J=7.3 Hz, 3H); $^{13}$C NMR (acetone D$_6$) 177.01, 79.28, 44.44, 40.92, 29.08, 15.50. Elemental analysis calc'd. for C$_9$H$_{17}$NO$_4$: C, 53.19, H, 8.42; N, 6.89. Found: C, 53.36; H, 8.46; N, 6.99.

I. Preparation of N-4-Methoxybenzyloxycarbonyl α-Methyl βAlanine

A solution of N-4-methoxybenzyloxycarbonyl α-methyl β-alanine methyl ester (2.81 g, 10.0 mmol) in 30 mL of 25% aqueous methanol was treated with lithium hydroxide (1.3 equivalents) at room temperature for a period of 2 h. The solution was concentrated in vacuo and the residue taken up in a mixture of water and ether and the phases separated and the organic phase discarded. The aqueous phase was acidified with aqueous potassium hydrogen sulfate to pH=1.5 and then extracted three times with ether. The combined ethereal phase was washed with saturated aqueous sodium chloride solution, dried over anhydrous magnesium sulfate, filtered and concentrated in vacuo to give 2.60 g, 97% of N-4-Methoxybenzyloxycarbonyl α-methyl β-alanine (N-Moz-AMBA) which was purified by recrystallization from a mixture of ethyl acetate and hexane to give 2.44 g, 91% of pure product, mp 96–97° C., MH+=268. $^1$H NMR (D$_6$-acetone/300 MHz) 1.16 (3H, d, J=7.2 Hz), 2.70 (1H, m), 3.31 (2H, m), 3.31 (3H, s), 4.99 (2H, s), 6.92 (2H, 4, J=8.7 Hz), 7.13 (2H, d, J=8.7 Hz).

EXAMPLE 7

Following generally the procedure of Example 6, or utilizing procedures known in the art, the β-amino acids set forth in Table 1 were prepared.

TABLE 1

| Entry | $R^1$ | $R^{1'}$ | $R^{1''}$ |
|---|---|---|---|
| 1 | —CH$_3$ | H | H |
| 2 | —CH(CH$_3$)$_2$ | H | H |
| 3 | —C(CH$_3$)$_3$ | H | H |
| 4 | H | H | H |
| 5 | H | —CH$_3$ | H |
| 6 | H | —CH$_3$ | —CH$_3$ |
| 7 | H | H | —CO$_2$CH$_3$ |
| 8 | H | H | —CONH$_2$ |
| 9 | —CH$_2$CH$_3$ | H | H |
| 10 | —CH$_2$CH(CH$_3$)$_2$ | H | H |
| 11 | —CH$_2$C$_6$H$_5$ | H | H |
| 12 | —CH$_2$—C$_6$H$_4$—OH | H | H |
| 13 | —CH$_2$—C$_6$H$_{11}$ | H | H |
| 14 | —CH$_2$COOH | H | H |
| 15 | H | —CH(CH$_3$)$_2$ | H |
| 16 | H | —CH$_2$CH(CH$_3$)$_2$ | H |
| 17 | H | —CH$_2$—C$_6$H$_5$ | H |
| 18 | H | —CH$_2$CH$_2$—C$_6$H$_5$ | H |
| 19 | H | —(CH$_2$)$_3$—C$_6$H$_5$ | H |
| 20 | H | —(CH$_2$)$_4$—C$_6$H$_5$ | H |
| 21 | H | —(CH$_2$)$_3$CH(C$_6$H$_5$)$_2$ | H |

EXAMPLE 8

Utilizing generally the procedure set forth in Example 6, the following β-amino acid compounds were prepared.

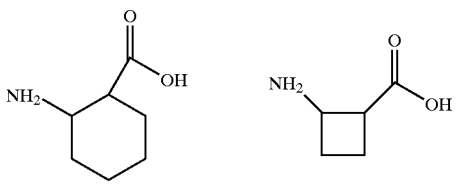

EXAMPLE 9

N[3(s)-benzyloxycarbonylamino-2(R)-hydroxy-4-phenylbutyl]-N-isobutylamine (370 mg. 1.0 mmole), prepared as in Example 3, is mixed with DIEA (280 μL, 2.0 mmoles) and 1.0 mmole of the sulfamoyl chloride derivative of methyl aminoisobutyrate (2 mmol) in a 100 mL round bottomed flask equipped with a reflux condenser, nitrogen inlet, and magnetic stir bar. The slurry is warmed to reflux and maintained at this temperature for about 1 hour or is stirred at room temperature for about two days.

A solution of this product (1 mmole) containing 20 mL of methanol and 5 mL of acetic acid is hydrogenated over 10% palladium on carbon (80 mg) for 6 h.

The free amine (0.2 mmoles) is then coupled with N-CBZ-L-asparagine (0.3 mmoles) in the presence of N-hydroxybenzotriazole (0.3 mmoles) and EDC (0.3 mmoles) to yield product.

EXAMPLE 10

Following the procedures of Examples 1–9, the compounds shown in Tables 2–14 could be prepared.

TABLE 2

| Entry No. | R | $R^1$ | $R^3$ | $R^{16}$ |
|---|---|---|---|---|
| 1 | Cbz | t-Butyl | i-Amyl | H |
| 2 | Q | t-Butyl | i-Amyl | Methyl |
| 3 | Cbz | i-Butyl | i-Butyl | Ethyl |
| 4 | N,N-Dimethylglycine | t-Butyl | i-Butyl | iso-Propyl |
| 5 | N,N-Dimethylglycine | t-Butyl | i-Butyl | t-Butyl |
| 6 | 2-Quinolinylcarbonyl | $CH_2C(O)NH_2$ | i-Butyl | Benzyl |
| 7 | 2-Quinolinylcarbonyl | $CH_2C(O)NH_2$ | i-Butyl | Methyl |
| 8 | 2-Quinolinylcarbonyl | $CH_2C(O)NH_2$ | i-Butyl | Hydrogen |

TABLE 3

| Entry No. | R | $R^3$ | $R^{16}$ |
|---|---|---|---|
| 1 | Cbz[a] | $CH_3$ | H |
| 2 | Cbz | i-Butyl | $CH_3$ |
| 3 | Cbz | i-Butyl | $CH_2CH_3$ |
| 4 | Q[b] | i-Butyl | $CH(CH_3)_2$ |
| 5 | Cbz | i-Propyl | $C(CH_3)_3$ |
| 6 | Q | i-Propyl | $CH_2Ph$ |
| 7 | Cbz | $C_6H_5$ | H |
| 8 | Cbz | —$CH_2$—cyclohexyl | $CH_3$ |
| 9 | Cbz | —$CH_2$—phenyl | $C(CH_3)_3$ |
| 10 | Q | —$CH_2$—phenyl | H |
| 11 | Cbz | cyclohexyl | $CH_2CH_3$ |
| 12 | Cbz | i-Butyl | $C(CH_3)_3$ |
| 13 | Cbz | i-Butyl | H |

TABLE 3-continued

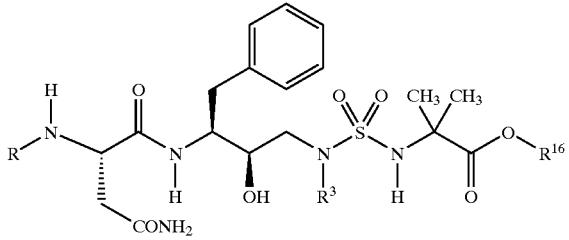

| Entry No. | R | R³ | R¹⁶ |
|---|---|---|---|
| 14 | Cbz | (R)—CH(CH₃)—C₆H₅ 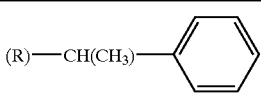 | CH₃ |
| 15 | Cbz | —CH₂—cyclohexyl 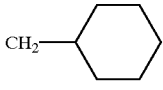 | CH₂CH₃ |
| 16 | Cbz | —CH₂—cyclohexyl 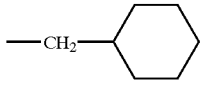 | CH(CH₃)₂ |
| 17 | Cbz | i-Butyl | C(CH₃)₃ |
| 18 | Cbz | i-Butyl | CH₂Ph |
| 19 | Cbz | i-amyl | H |
| 20 | Q | -Butyl | CH₃ |
| 21 | Cbz | —CH₂—cyclohexyl 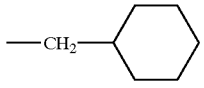 | C(CH₃)₃ |
| 22 | Cbz | (CH₂)₂CH(CH₃)₂ | H |
| 23 | Q | i-Butyl | CH₂CH₃ |
| 24 | Cbz | i-amyl | C(CH₃)₃ |
| 25 | Q | i-Butyl | H |
| 26 | Cbz | —CH₂—naphthyl 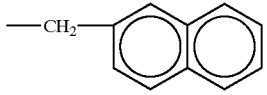 | CH₃ |
| 27 | Q | —CH₂—naphthyl 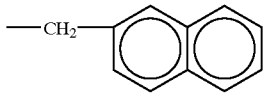 | CH₂CH₃ |
| 28 | Cbz | —(CH₂)₂CH(CH₃)₂ | CH(CH₃)₂ |
| 29 | Q | —(CH₂)₂CH(CH₃)₂ | C(CH₃)₃ |
| 30 | Cbz | —CH₂C₆H₅ | CH₂Ph |
| 31 | β-naphthylcarbonyl | —CH₂C₆H₅ | H |
| 32 | Cbz | —(CH₂)₂C₆H₅ | CH₃ |
| 33 | Cbz | —(CH₂)₂C₆H₅ | C(CH₃)₃ |
| 34 | Cbz | n-Butyl | H |
| 35 | Cbz | n-Pentyl | CH₂CH₃ |
| 36 | Cbz | n-Hexyl | C(CH₃)₃ |
| 37 | Cbz | —CH₂—C₆H₅ 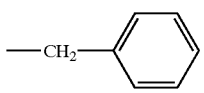 | H |
| 38 | β-naphthylcarbonyl | —CH₂C(CH₃)₃ | CH₃ |
| 39 | β-naphthylcarbonyl | —CH₂C(CH₃)₃ | CH₂CH₃ |
| 40 | Cbz | —CH₂CH₂—morpholinyl 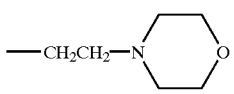 | CH(CH₃)₂ |

TABLE 3-continued

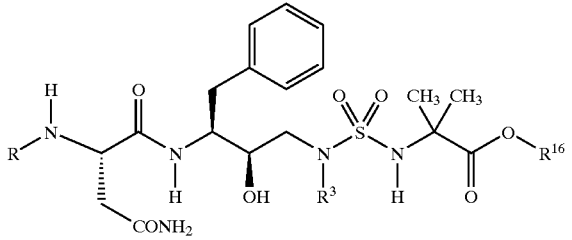

| Entry No. | R | R³ | R¹⁶ |
|---|---|---|---|
| 41 | Cbz | —CH₂C₆H₅OCH₃(para) | C(CH₃)₃ |
| 42 | Cbz | —CH₂-(3-pyridyl) | CH₂Ph |
| 43 | Cbz | —CH₂-(4-pyridyl) | H |
| 44 | Cbz | —(CH₂)₂C(CH₃)₃ | CH₃ |
| 45 | Q | —(CH₂)₂C(CH₃)₃ | C(CH₃)₃ |
| 46 | Cbz | —(CH₂)₄OH | H |
| 47 | Q | —(CH₂)₄OH | CH₂CH₃ |
| 48 | Q | —CH₂-(4-F-C₆H₄) | C(CH₃)₃ |
| 49 | Q | —CH₂-(4-pyridyl) | H |
| 50 | Cbz | —CH₂CH(CH₃)₂ | CH₃ |
| 51 | 3-acetyl-quinolinyl | —CH₂CH₂CH(CH₃)₂ | CH₂CH₃ |
| 52 | (CH₃)₂NCH₂C(O)CH₃- | —CH₂CH(CH₃)₂ | CH(CH₃)₂ |
| 53 | pyrimidin-2-yl-S-CH₂C(O)- | —CH₂CH(CH₃)₂ | C(CH₃)₃ |
| 54 | benzofuran-2-yl-C(O)- | —CH₂CH(CH₃)₂ | CH₂Ph |
| 55 | CH₃C(O)- | —CH₂CH(CH₃)₂ | H |

TABLE 3-continued

[Structure: R-NH-CH(CH2CONH2)-C(=O)-NH-CH(CH2Ph)-CH(OH)-CH2-N(R3)-S(=O)2-NH-C(CH3)2-C(=O)-O-R16]

| Entry No. | R | R³ | R¹⁶ |
|---|---|---|---|
| 56 | 5-acetyl-1H-benzimidazole | —CH₂CH(CH₃)₂ | CH₃ |
| 57 | 2-acetylpyridine | —CH₂CH(CH₃)₂ | C(CH₃)₃ |
| 58 | 3-hydroxyquinoxaline-2-carbaldehyde | —CH₂CH(CH₃)₂ | H |
| 59 | 2-acetyl-3-hydroxypyridine | —CH₂CH(CH₃)₂ | CH₂CH₃ |
| 60 | 2-acetyl-1H-benzimidazole | —CH₂CH(CH₃)₂ | C(CH₃)₃ |
| 61 | 6-acetylquinoline | —CH₂CH(CH₃)₂ | H |
| 62 | 3-acetylisoquinoline | —CH₂CH(CH₃)₂ | CH₃ |
| 63 | 3-acetylquinoline | —CH₂CH(CH₃)₂ | CH₂CH₃ |

TABLE 3-continued
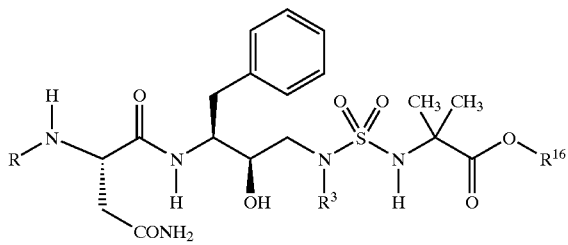
| Entry No. | R | R³ | R¹⁶ |
|---|---|---|---|
| 64 | 2-acetyl-quinoxaline | —CH₂CH(CH₃)₂ | CH(CH₃)₂ |
| 65 | 4-acetyl-quinoline | —CH₂CH(CH₃)₂ | C(CH₃)₃ |
| 66 | 3-amino-2-acetyl-naphthalene | —CH₂CH(CH₃)₂ | CH₂Ph |
| 67 | 1-acetyl-isoquinoline | —CH₂CH(CH₃)₂ | H |
| 68 | 2-amino-acetophenone | —CH₂CH(CH₃)₂ | CH₃ |
| 69 | 1-hydroxy-2-acetyl-naphthalene | —CH₂CH(CH₃)₂ | C(CH₃)₃ |
| 70 | 3-acetyl-quinoline | —CH₂Ph | H |
| 71 | Q | —CH₂-(4-F-C₆H₄) | CH₂CH₃ |

TABLE 3-continued

| Entry No. | R | R³ | R¹⁶ |
|---|---|---|---|
| 72 | Q | —CH₂-cyclohexyl | C(CH₃)₃ |
| 73 | Q | —CH₂-(4-methoxyphenyl) | H |
| 74 | Q | —CH₂-(pyridyl) | CH₃ |
| 75 | Q | —CH₂-cyclopropyl | H |
| 76 | Q | —CH₂CH=CH₂ | CH₃ |
| 77 | Q | —phenyl | CH₂CH₃ |
| 78 | Q | —cyclohexyl | CH(CH₃)₂ |
| 79 | Q | —CH₂CH₂Ph | C(CH₃)₃ |
| 80 | Q | —CH₂CH₂CH₂CH₂OH | CH₂Ph |
| 81 | Q | —CH₂CH₂N(CH₃)₂ | H |
| 82 | Q | —CH₂CH₂-morpholinyl | CH₃ |
| 83 | Q | —CH₃ | C(CH₃)₃ |
| 84 | Q | —CH₂CH₂CH₂SCH₃ | H |
| 85 | Q | —CH₂CH₂CH₂S(O)₂CH₃ | CH₂CH₃ |
| 86 | Q | —CH₂CH₂CH₂CH(CH₃)₂ | C(CH₃)₃ |
| 87 | Q | —CH₂CH₂CH(CH₃)₂ | H |
| 88 | Q | —CH₂CH₂CH(CH₃)₂ | CH₃ |
| 89 | Q | —CH₂CH₂CH₂CH(CH₃)₂ | CH₂CH₃ |
| 90 | Q | —CH₂CH₂CH(CH₃)₂ | CH(CH₃)₂ |
| 91 | Q | —CH₂CH₂CH(CH₃)₂ | C(CH₃)₃ |
| 92 | Q | —CH₂CH₂CH(CH₃)₂ | CH₂Ph |
| 93 | Q | —CH₂CH₂CH(CH₃)₂ | H |
| 94 | β-naphthylcarbonyl | —CH₂CH₂CH(CH₃)₂ | H |
| 95 | β-naphthylcarbonyl | —CH₂CH₂CH(CH₃)₂ | CH₃ |
| 96 | Q | —CH₂CH(CH₃)₂ | CH₂CH₃ |
| 97 | β-naphthylcarbonyl | —CH₂CH₂CH(CH₃)₂ | CH(CH₃)₂ |
| 98 | β-naphthylcarbonyl | —CH₂CH₂CH(CH₃)₂ | C(CH₃)₃ |
| 99 | β-naphthylcarbonyl | —CH₂CH₂CH(CH₃)₂ | CH₂Ph |
| 100 | β-naphthylcarbonyl | —CH₂CH₂CH(CH₃)₂ | H |
| 101 | β-naphthylcarbonyl | —CH₂CH₂CH(CH₃)₂ | CH₃ |
| 102 | Q | —CH₂CH₂CH(CH₃)₂ | C(CH₃)₃ |
| 103 | β-naphthylcarbonyl | —CH₂CH(CH₃)₂ | H |
| 104 | Q | —CH₂CH(CH₃)₂ | CH₂CH₃ |
| 105 | Q | —CH₂CH(CH₃)₂ | C(CH₃)₃ |
| 106 | Q | —CH₂CH₂CH₃ | H |

TABLE 3-continued

[Structure: peptide with R-NH-CH(CH2CONH2)-C(=O)-NH-CH(CH2Ph)-CH(OH)-CH2-N(R3)-S(=O)2-NH-C(CH3)2-C(=O)-O-R16]

| Entry No. | R | R$^3$ | R$^{16}$ |
|---|---|---|---|
| 107 | β-naphthylcarbonyl | —CH$_2$CH$_2$CH$_2$CH$_3$ | CH$_3$ |
| 108 | Q | —CH$_2$CH$_2$CH$_3$ | CH$_2$CH$_3$ |
| 109 | Q | —CH$_2$CH$_2$CH$_3$ | CH(CH$_3$)$_2$ |
| 110 | Q | —CH$_2$CH$_2$CH$_3$ | C(CH$_3$)$_3$ |
| 111 | Q | —CH$_2$CH$_2$CH$_3$ | CH$_2$Ph |

[a] benzyloxycarbonyl
[b] 2-quinolinylcarbonyl

TABLE 4

[Structure: Q—ASN—NH—CH(CH2Ph)—CH(OH)—CH2—N(R3)—S(=O)2—NH—C(CH3)2—(CH2)n—R8]

| n | R$^3$ | R$^8$ |
|---|---|---|
| 0 | —CH$_2$CH(CH$_3$)$_2$ | —CN |
| 0 | —CH$_2$CH$_2$CH(CH$_3$)$_2$ | phenyl |
| 1 | —CH$_2$CH$_2$CH(CH$_3$)$_2$ | phenyl |
| 1 | —CH$_2$CH$_2$CH(CH$_3$)$_2$ | —C(O)N(CH$_3$)$_2$ |
| 1 | —CH$_2$CH$_2$CH(CH$_3$)$_2$ | —CO$_2$CH$_3$ |
| 2 | —CH$_2$CH$_2$CH(CH$_3$)$_2$ | phenyl |
| 1 | —CH$_2$-(4-pyridyl) | phenyl |
| 1 | —CH$_2$-(4-pyridyl) | 4-pyridyl |
| 0 | —CH$_2$CH$_2$CH(CH$_3$)$_2$ | —C(O)CH$_3$ |
| 0 | —CH$_2$-(4-F-phenyl) | —C(O)CH$_3$ |
| 1 | —CH$_2$-(4-F-phenyl) | 4-pyridyl |
| 1 | —CH$_2$CH(CH$_3$)$_2$ | OH |
| 1 | —CH$_2$-(4-F-phenyl) | OH |
| 2 | —CH$_2$-(4-F-phenyl) | morpholino |
| 2 | —CH$_2$-(4-F-phenyl) | piperidino |
| 1 | —CH$_2$-(4-F-phenyl) | —SCH$_3$ |
| 1 | —CH$_2$-(4-F-phenyl) | —SO$_2$CH$_3$ |

TABLE 4-continued

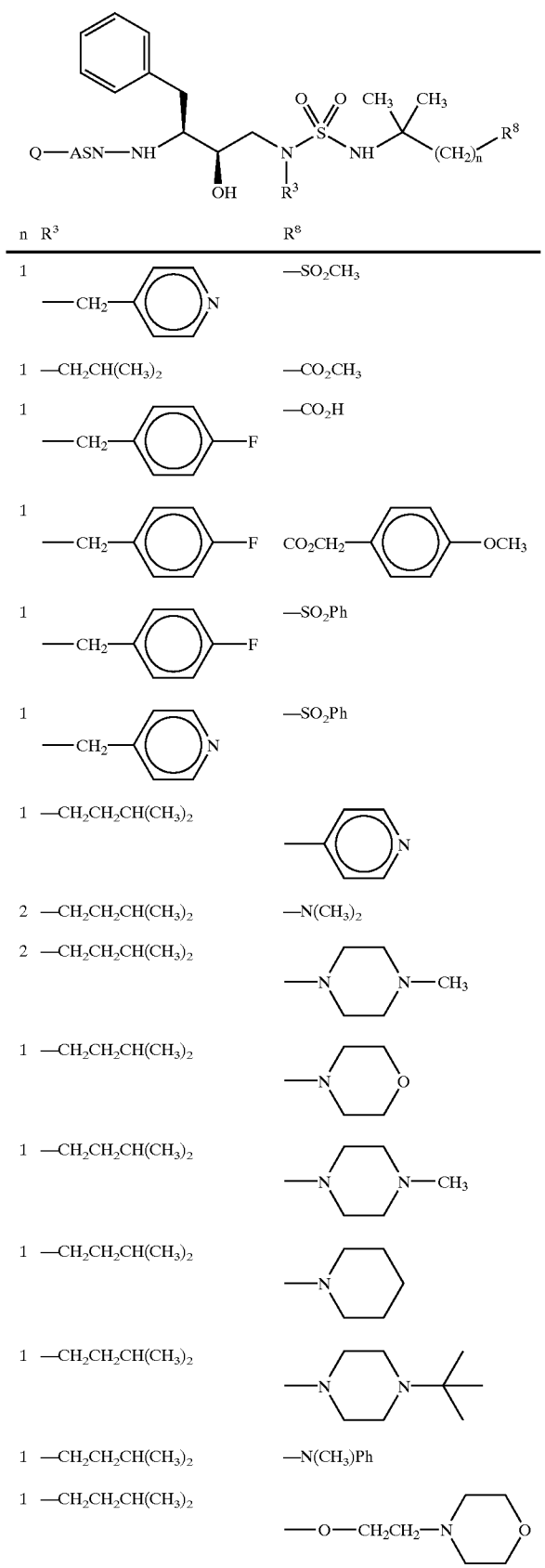

| n | R³ | R⁸ |
|---|---|---|
| 1 | —CH₂-(4-pyridyl) | —SO₂CH₃ |
| 1 | —CH₂CH(CH₃)₂ | —CO₂CH₃ |
| 1 | —CH₂-(4-F-phenyl) | —CO₂H |
| 1 | —CH₂-(4-F-phenyl) | —CO₂CH₂-(4-OCH₃-phenyl) |
| 1 | —CH₂-(4-F-phenyl) | —SO₂Ph |
| 1 | —CH₂-(4-pyridyl) | —SO₂Ph |
| 1 | —CH₂CH₂CH(CH₃)₂ | —(4-methylpyridyl) |
| 2 | —CH₂CH₂CH(CH₃)₂ | —N(CH₃)₂ |
| 2 | —CH₂CH₂CH(CH₃)₂ | —N-methylpiperazinyl |
| 1 | —CH₂CH₂CH(CH₃)₂ | —morpholinyl |
| 1 | —CH₂CH₂CH(CH₃)₂ | —N-methylpiperazinyl |
| 1 | —CH₂CH₂CH(CH₃)₂ | —piperidinyl |
| 1 | —CH₂CH₂CH(CH₃)₂ | —N-t-butylpiperazinyl |
| 1 | —CH₂CH₂CH(CH₃)₂ | —N(CH₃)Ph |
| 1 | —CH₂CH₂CH(CH₃)₂ | —O—CH₂CH₂-morpholinyl |

TABLE 4-continued

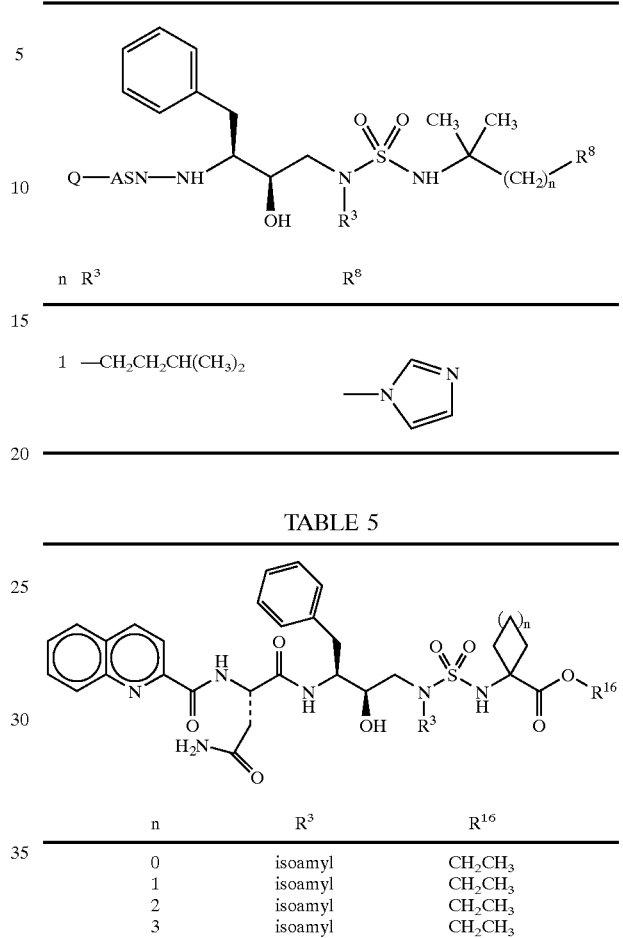

| n | R³ | R⁸ |
|---|---|---|
| 1 | —CH₂CH₂CH(CH₃)₂ | N-methylimidazolyl |

TABLE 5

| n | R³ | R¹⁶ |
|---|---|---|
| 0 | isoamyl | CH₂CH₃ |
| 1 | isoamyl | CH₂CH₃ |
| 2 | isoamyl | CH₂CH₃ |
| 3 | isoamyl | CH₂CH₃ |

TABLE 6

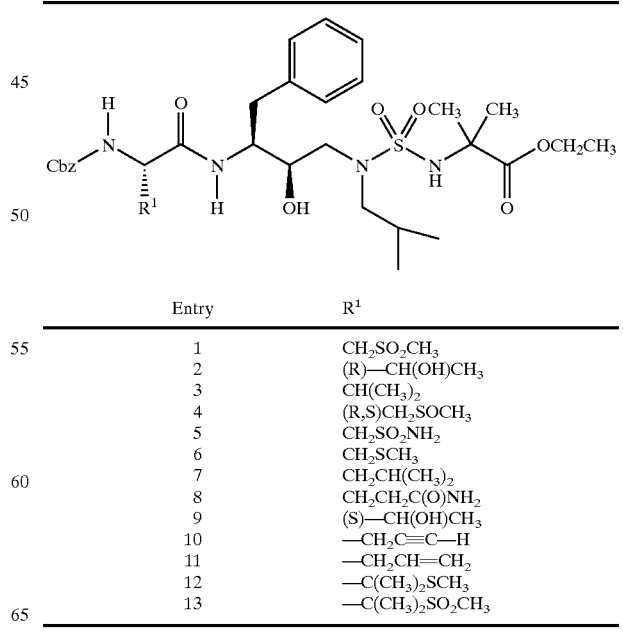

| Entry | R¹ |
|---|---|
| 1 | CH₂SO₂CH₃ |
| 2 | (R)—CH(OH)CH₃ |
| 3 | CH(CH₃)₂ |
| 4 | (R,S)CH₂SOCH₃ |
| 5 | CH₂SO₂NH₂ |
| 6 | CH₂SCH₃ |
| 7 | CH₂CH(CH₃)₂ |
| 8 | CH₂CH₂C(O)NH₂ |
| 9 | (S)—CH(OH)CH₃ |
| 10 | —CH₂C≡C—H |
| 11 | —CH₂CH=CH₂ |
| 12 | —C(CH₃)₂SCH₃ |
| 13 | —C(CH₃)₂SO₂CH₃ |

TABLE 7

| Entry | R² | A |
|---|---|---|
| 1 | n-Bu | Cbz-Asn |
| 2 | cyclohexylmethyl | Cbz-Asn |
| 3 | n-Bu | Boc |
| 4 | n-Bu | Cbz |
| 5 | C₆H₅CH₂ | Boc |
| 6 | P—F—C₆H₅CH₂ | Cbz |
| 7 | C₆H₅CH₂ | benzoyl |
| 8 | cyclohexylmethyl | Cbz |
| 9 | n-Bu | Q-Asn |
| 10 | cyclohexylmethyl | Q-Asn |
| 11 | C₆H₅CH₂ | Cbz-Ile |
| 12 | C₆H₅CH₂ | Q-Ile |
| 13 | P—F—C₆H₅CH₂ | Cbz-t-BuGly |
| 14 | C₆H₅CH₂ | Q-t-BuGly |
| 15 | C₆H₅CH₂ | Cbz-Val |
| 16 | C₆H₅CH₂ | Q-Val |
| 17 | 2-naphthylmethyl | Cbz-Asn |
| 18 | 2-naphthylmethyl | Q-Asn |
| 19 | 2-naphthylmethyl | Cbz |
| 20 | n-Bu | Cbz-Val |
| 21 | n-Bu | Q-Val |
| 22 | n-Bu | Q-Ile |
| 23 | n-Bu | Cbz-t-BuGly |
| 24 | n-Bu | Q-t-BuGly |
| 25 | p-F(C₆H₄)CH₂ | Q-Asn |
| 26 | p-F(C₆H₄)CH₂ | Cbz |
| 27 | p-F(C₆H₄)CH₂ | Cbz-Asn |
| 28 | C₆H₅CH₂ | Cbz-propargylglycine |
| 29 | C₆H₅CH₂ | Q-propargylglycine |
| 30 | C₆H₅CH₂ | acetylpropargylglycine |
| 31 | n-Bu | dimethylglycyl-t-butylglycine |
| 32 | n-Bu | dimethylglycyl-isoleucine |
| 33 | n-Bu | dimethylglycyl-valine |
| 34 | —CH₂CH₂SCH₃ | dimethylglycyl-t-butylglycine |
| 35 | —CH₂CH₂SCH₃ | dimethylglycyl-isoleucine |
| 36 | —CH₂CH₂SCH₃ | dimethylglycyl-valine |

TABLE 8

| Entry | R | R¹ |
|---|---|---|
| 1 | 4-methoxybenzyl acetate group | —CH₃ |
| 2 | acetyl | —CH₃ |

TABLE 8-continued

[Structure shown: R-NH-CH(R¹)-C(=O)-NH-CH(CH₂Ph)-CH(OH)-CH₂-N(isopentyl)-S(=O)(OCH₃)-NH-C(CH₃)(OCH₂CH₃)-C(=O) with the central sulfonyl group bearing OCH₃, and terminal group containing CH₃ and OCH₂CH₃]

| Entry | R | R¹ |
|---|---|---|
| 3 | 4-CH₃O-C₆H₄-CH₂-O-C(=O)- | —CH(CH₃)₂ |
| 4 | CH₃-C(=O)- | —CH(CH₃)₂ |
| 5 | C₆H₅-CH₂-O-C(=O)- | —C(CH₃)₃ |
| 6 | 2-naphthyl-O-CH₂-C(=O)- | —CH₃ |
| 7 | C₆H₅-O-CH₂-C(=O)- | —CH₃ |
| 8 | HO₂CCH₂CH₂-C(=O)- | —CH₃ |
| 9 | C₆H₅-C(=O)- | —CH₃ |
| 10 | CH₃NH-C(=O)- | —CH₃ |
| 11 | (CH₃)₂CH-C(=O)- | —CH₃ |
| 12 | CH₃OCH₂-C(=O)- | —CH₃ |
| 13 | (CH₃)₂NCH₂-C(=O)- | —CH₃ |

TABLE 8-continued

| Entry | R | R¹ |
|---|---|---|
| 14 | CH₃CH(OH)—C(O)— | —CH₃ |
| 15 | (4-methoxybenzyl)OC(O)NH-cyclohexyl structure | |
| 16 | (benzyl)OC(O)NH-cyclobutyl structure | |

TABLE 9

| Entry | R¹ | R¹' | R¹" | R |
|---|---|---|---|---|
| 1 | H | H | H | PhCH₂O—C(O)— |
| 2 | H | H | H | CH₃—C(O)— |

TABLE 9-continued

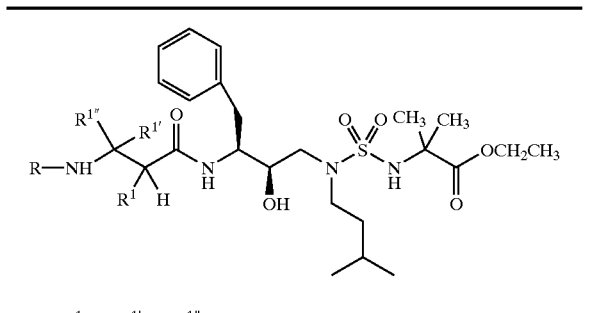

| Entry | R¹ | R¹' | R¹" | R |
|---|---|---|---|---|
| 3 | H | CH₃ | H | CH₃O-C₆H₄-CH₂O-C(=O)- |
| 4 | H | CH₃ | CH₃ | C₆H₅-CH₂O-C(=O)- |
| 5 | H | H | CO₂CH₃ | C₆H₅-CH₂O-C(=O)- |
| 6 | H | H | H | CH₃O-C₆H₄-CH₂O-C(=O)- |
| 7 | H | H | H | H₂N-C(=O)- |
| 8 | H | H | CONH₂ | Cbz |
| 9 | H | H | CONH₂ | 2-quinolinylcarbonyl |

TABLE 10

| Entry | R | R' | X |
|---|---|---|---|
| 1 | R = H | R' = H | X = H |
| 2 | R = Me | R' = Me | X = H |
| 3 | R = H | R' = Me | X = H |
| 4 | R = Me | R' = Me | X = F |
| 5 | R = H | R' = Me | X = F |
| 6 | R = Cbz | R' = Me | X = H |
| 7 | R = H | R' = Bz | X = H |
| 8 | R + R' = pyrrole | | X = H |

TABLE 11

| Entry | Acyl Group (R) |
|---|---|
| 1 | benzyloxycarbonyl |
| 2 | tert-butoxycarbonyl |
| 3 | acetyl |
| 4 | 2-quinoylcarbonyl |
| 5 | phenoxyacetyl |
| 6 | benzoyl |
| 7 | methyloxaloyl |
| 8 | pivaloyl |
| 9 | trifluoracetyl |
| 10 | bromoacetyl |
| 11 | hydroxyacetyl |
| 12 | morpholinylacetyl |
| 13 | N,N-dimethylaminoacetyl |
| 14 | N-benzylaminoacetyl |
| 15 | N-phenylaminoacetyl |
| 16 | N-benzyl-N-methylaminoacetyl |
| 17 | N-methyl-N-(2-hydroxyethyl)aminoacetyl |
| 18 | N-methylcarbamoyl |
| 19 | 3-methylbutyryl |
| 20 | N-isobutylcarbamoyl |
| 21 | succinoyl (3-carboxypropionyl) |
| 22 | carbamoyl |
| 23 | N-(2-indanyl)aminoacetyl |

TABLE 12

| Entry | R³ | R¹⁶ |
|---|---|---|
| 1 | —CH₃ | H |
| 2 | -i-Butyl | CH₃ |
| 3 | -i-Butyl | CH₂CH₃ |
| 4 | -i-Propyl | CH(CH₃)₂ |
| 5 | —C₆H₅ | C(CH₃)₃ |
| 6 | —CH₂-cyclohexyl | CH₂Ph |
| 7 | —CH₂-phenyl | H |

TABLE 12-continued

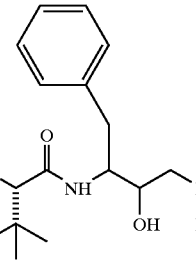

| Entry | R³ | R¹⁶ |
|---|---|---|
| 8 | methylcyclohexyl (—CH(CH₃)-cyclohexyl) | CH₃ |
| 9 | -i-Butyl | C(CH₃)₃ |
| 10 | -i-Butyl | H |
| 11 | —(R)—CH(CH₃)—C₆H₅ | CH₂CH₃ |
| 12 | —CH₂-cyclohexyl | C(CH₃)₃ |
| 13 | —CH₂-cyclohexyl | H |
| 14 | n-propyl | CH₃ |
| 15 | n-propyl | CH₂CH₃ |
| 16 | i-Butyl | CH(CH₃)₂ |
| 17 | —CH₂-cyclohexyl | C(CH₃)₃ |
| 18 | (CH₂)₂CH(CH₃)₂ | CH₂Ph |
| 19 | i-propyl | H |
| 20 | i-propyl | CH₃ |
| 21 | —CH₂-naphthyl | C(CH₃)₃ |
| 22 | —(CH₂)₂CH(CH₃)₂ | H |
| 23 | —CH₂C₆H₅ | CH₂CH₃ |
| 24 | —(CH₂)₂C₆H₅ | C(CH₃)₃ |
| 25 | n-Butyl | H |
| 26 | n-Pentyl | CH₃ |
| 27 | n-Hexyl | CH₂CH₃ |
| 28 | —CH₂-phenyl | CH(CH₃)₂ |
| 29 | —CH₂C(CH₃)₃ | C(CH₃)₃ |
| 30 | —CH₂CH₂-morpholinyl | CH₂Ph |
| 31 | —CH₂C₆H₅OCH₃(para) | H |

TABLE 12-continued

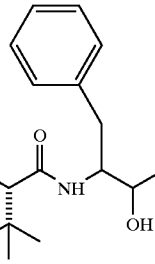

| Entry | R³ | R¹⁶ |
|---|---|---|
| 32 | —CH₂-(3-pyridyl) | CH₃ |
| 33 | —CH₂-(4-pyridyl) | C(CH₃)₃ |
| 34 | —(CH₂)₂C(CH₃)₃ | H |
| 35 | —(CH₂)₄OH | CH₂CH₃ |
| 36 | —CH₂-(4-fluorophenyl) | C(CH₃)₃ |
| 37 | —CH₂-(4-pyridyl) | H |
| 38 | —CH₂CH₂CH₂SCH₃ | CH₃ |
| 39 | i-amyl | CH₂CH₃ |
| 40 | methylcyclohexyl | CH(CH₃)₂ |
| 41 | —CH₂-cyclohexyl | CH₂C(CH₃)₃ |
| 42 | i-butyl | CH₂Ph |
| 43 | —CH₂Ph | —CH₂Ph |
| 44 | —CH₂-(4-fluorophenyl) | CH₃ |
| 45 | —CH₂-(4-fluorophenyl) | —CH₂Ph |
| 46 | —CH₂-(4-methoxyphenyl) | CH₃ |
| 47 | —CH₂-(4-pyridyl) | CH₂CH₃ |
| 48 | —CH₂-cyclopropyl | C(CH₃)₃ |

TABLE 12-continued

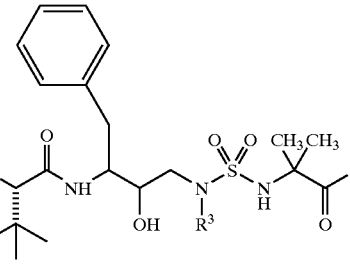

| Entry | R³ | R¹⁶ |
|---|---|---|
| 49 | —CH₂CH=CH₂ | H |
| 50 | 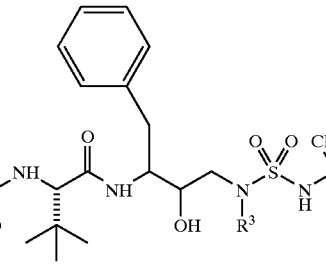 (phenyl) | CH₃ |
| 51 | 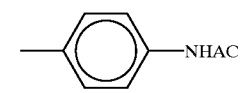 (cyclohexyl) | CH₂CH₃ |
| 52 | —CH₂CH₂Ph | CH(CH₃)₂ |
| 53 | —CH₂CH₂CH₂CH₂OH | C(CH₃)₃ |
| 54 | —CH₂CH₂N(CH₃)₂ | CH₂Ph |
| 55 | —CH₂CH₂—N(morpholine) 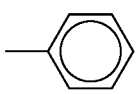 | H |
| 56 | —CH₃ | CH₃ |
| 57 | —CH₂CH₂CH₂SCH₃ | C(CH₃)₃ |
| 58 | —CH₂CH₂CH₂S(O)₂CH₃ | H |
| 59 | —CH₂CH₂CH₂CH₃ | CH₂CH₃ |
| 60 | —CH₂CH₂CH₂CH₃ | C(CH₃)₃ |
| 61 | —CH₂CH₂CH₂CH₃ | H |
| 62 | —CH₂CH₂CH₂CH₃ | CH₃ |
| 63 | —CH₂CH₂CH₂CH₃ | CH₂CH₃ |
| 64 | —CH₂CH₂CH₂CH₃ | CH(CH₃)₂ |
| 65 | —CH₂CH₂CH₂CH₃ | C(CH₃)₃ |
| 66 | —CH₂CH₂CH₂CH₃ | CH₂Ph |
| 67 | —CH₂CH₂CH₂CH₃ | H |
| 68 | —CH₂CH₂CH₂CH₃ | CH₃ |
| 69 | —CH₂CH₂CH₂CH₃ | C(CH₃)₃ |
| 70 | —CH₂CH₂CH₂CH₃ | H |
| 71 | —CH₂CH₂CH₂CH₃ | CH₂CH₃ |
| 72 | —CH₂CH₂CH₂CH₃ | C(CH₃)₃ |
| 73 | —CH₂CH₂CH₂CH₃ | 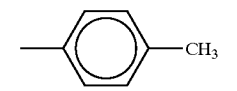 (2,4-dimethylphenyl) |
| 74 | —CH₂CH₂CH(CH₃)₂ | 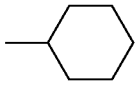 (2-methylbenzyl CO₂CH₃) |
| 75 | —CH₂CH(CH₃)₂ | 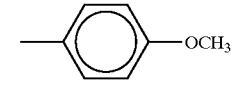 (phenyl) |
| 76 | —CH₂CH(CH₃)₂ | 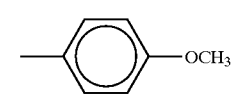 (4-F-phenyl) |
| 77 | —CH₂CH(CH₃)₂ |  (4-NHAc-phenyl) |
| 78 | —CH₂CH(CH₃)₂ | 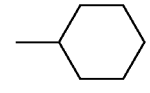 (4-CH₃-phenyl) |
| 79 | —CH₂CH₂CH₃ | 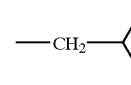 (4-OCH₃-phenyl) |
| 80 | —CH₂CH₂CH₂CH₃ | 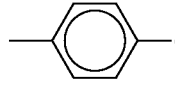 (4-OCH₃-phenyl) |
| 81 | i-butyl | t-butyl |
| 82 | i-amyl | t-butyl |
| 83 | 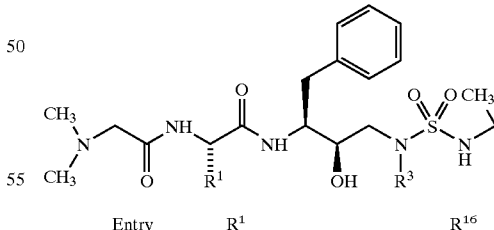 (cyclohexyl) | t-butyl |
| 84 | —CH₂— 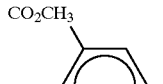 (cyclohexylmethyl) | t-butyl |

TABLE 13

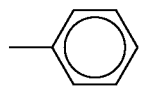

| Entry | R¹ | R¹⁶ |
|---|---|---|
| 1 | C(CH₃)₃ | H |
| 2 | CH₂C≡CH | CH₃ |
| 3 | C(CH₃)₂(SCH₃) | CH₂CH₃ |
| 4 | C(CH₃)₂(S[O]CH₃) | CH(CH₃)₂ |
| 5 | C(CH₃)₂(S[O]₂CH₃) | C(CH₃)₃ |
| 6 | C(CH₃)₃ | CH₂Ph |
| 7 | C(CH₃)₃ | CH₃ |
| 8 | CH(CH₃)₂ | CH₃ |
| 9 | CH(CH₂CH₃)(CH₃) | C(CH₃)₃ |

TABLE 14

[Structure: CH₃\N-CH₂-C(O)-NH-CH(R¹)-C(O)-NH-CH(R²)-CH(OH)-CH₂-N(R³)-S(O)₂-N(H)-C(CH₃)₂-CH₂-C(O)-OCH₃ with (CH₃)₂N- group]

| R¹ | R² | R³ |
| --- | --- | --- |
| t-Butyl | Benzyl | p-Fluorobenzyl |
| i-Butyl | Benzyl | i-Amyl |
| i-Propyl | Benzyl | i-Amyl |
| Propargyl | Benzyl | i-Amyl |
| t-Butyl | Benzyl | i-Amyl |
| t-Butyl | Benzyl | Benzyl |
| t-Butyl | Benzyl | n-Butyl |
| sec-Butyl | Benzyl | i-Amyl |
| C(CH₃)₂(SCH₃) | Benzyl | i-Amyl |
| t-Butyl | p-Fluorobenzyl | p-Methoxybenzyl |
| i-Butyl | p-Fluorobenzyl | i-Amyl |
| i-Propyl | p-Fluorobenzyl | i-Amyl |
| Propargyl | p-Fluorobenzyl | i-Amyl |
| t-Butyl | p-Fluorobenzyl | i-Amyl |
| t-Butyl | p-Fluorobenzyl | Benzyl |
| t-Butyl | p-Fluorobenzyl | n-Butyl |
| sec-Butyl | p-Fluorobenzyl | i-Amyl |
| C(CH₃)₂(SCH₃) | p-Fluorobenzyl | i-Amyl |
| t-Butyl | Cyclohexylmethyl | p-Fluorobenzyl |
| i-Butyl | Cyclohexylmethyl | i-Amyl |
| i-Propyl | Cyclohexylmethyl | i-Amyl |
| Propargyl | Cyclohexylmethyl | i-Amyl |
| t-Butyl | Cyclohexylmethyl | i-Amyl |
| t-Butyl | Cyclohexylmethyl | Benzyl |
| t-Butyl | Cyclohexylmethyl | n-Butyl |
| sec-Butyl | Cyclohexylmethyl | i-Amyl |
| C(CH₃)₂(SCH₃) | Cyclohexylmethyl | i-Amyl |
| t-Butyl | n-Butyl | Cyclohexylmethyl |
| i-Butyl | n-Butyl | i-Amyl |
| i-Propyl | n-Butyl | i-Amyl |
| Propargyl | n-Butyl | i-Amyl |
| t-Butyl | n-Butyl | i-Amyl |
| t-Butyl | n-Butyl | Benzyl |
| t-Butyl | n-Butyl | n-Butyl |
| sec-Butyl | n-Butyl | i-Amyl |
| C(CH₃)₂(SCH₃) | n-Butyl | i-Amyl |

EXAMPLE 11

The compounds of the present invention are effective HIV protease inhibitors. Utilizing an enzyme assay as described below, the compounds set forth in the examples herein would be expected to inhibit the HIV enzyme. The enzyme method is described below. The substrate is 2-Ile-Nle-Phe (p-NO₂)-Gln-ArgNH₂. The positive control is MVT-101 [Miller, M. et al, *Science*, 246, 1149 (1989)]. The assay conditions are as follows:

| Assay buffer: | 20 mM sodium phosphate, pH 6.4 |
| --- | --- |
| | 20% glycerol |
| | 1 mM EDTA |
| | 1 mM DTT |
| | 0.1% CHAPS |

The above described substrate is dissolved in DMSO, then diluted 10 fold in assay buffer. Final substrate concentration in the assay is 80 μM.

HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10x the test concentration; 10 μl of the enzyme preparation is added, the materials mixed and then the mixture is incubated at ambient temperature for 15 minutes. The enzyme reaction is initiated by the addition of 40 μl of substrate. The increase in fluorescence is monitored at 4 time points (0, 8, 16 and 24 minutes) at ambient temperature. Each assay is carried out in duplicate wells.

EXAMPLE 12

The effectiveness of the compounds can also be determined in a CEM cell assay.

The HIV inhibition assay method of acutely infected cells is an automated tetrazolium based calorimetric assay essentially that reported by Pauwles et al, *J. Virol. Methods*, 20, 309–321 (1988). Assays can be performed in 96-well tissue culture plates. CEM cells, a CD4⁺ cell line, were grown in RPMI-1640 medium (Gibco) supplemented with a 10% fetal calf serum and were then treated with polybrene (2 μg/ml). An 80 μl volume of medium containing 1×10⁴ cells is dispensed into each well of the tissue culture plate. To each well is added a 100 μl volume of test compound dissolved in tissue culture medium (or medium without test compound as a control) to achieve the desired final concentration and the cells are incubated at 37° C. for 1 hour. A frozen culture of HIV-1 is diluted in culture medium to a concentration of 5×10⁴ TCID₅₀ per ml (TCID₅₀ =the dose of virus that infects 50% of cells in tissue culture) and a 20 μL volume of the virus sample (containing 1000 TCID₅₀ of virus) is added to wells containing test compound and to wells containing only medium (infected control cells). Several wells receive culture medium without virus (uninfected control cells). Likewise, the intrinsic toxicity of the test compound is determined by adding medium without virus to several wells containing test compound. In summary, the tissue culture plates contain the following experiments:

| | Virus | Cells | Drug |
| --- | --- | --- | --- |
| 1. | + | − | − |
| 2. | + | + | − |
| 3. | + | − | + |
| 4. | + | + | + |

In experiments 2 and 4 the final concentrations of test compounds are 1, 10, 100 and 500 μg/ml. Either azidothymidine (AZT) or dideoxyinosine. (ddI) is included as a positive drug control. Test compounds are dissolved in DMSO and diluted into tissue culture medium so that the final DMSO concentration does not exceed 1.5% in any case. DMSO is added to all control wells at an appropriate concentration.

Following the addition of virus, cells are incubated at 37° C. in a humidified, 5% CO₂ atmosphere for 7 days. Test compounds could be added on days 0, 2 and 5 if desired. On day 7, post-infection, the cells in each well are resuspended and a 100 μl sample of each cell suspension is removed for assay. A 20 μL volume of a 5 mg/ml solution of 3-(4,5-dimethylthiazol-2-yl)-2,5-diphenyltetrazolium bromide (MTT) is added to each 100 μL cell suspension, and the cells are incubated for 4 hours at 27° C. in a 5% CO₂ environment. During this incubation, MTT is metabolically reduced by living cells resulting in. the production in the cell of a colored formazan product. To each sample is added 100 μl of 10% sodium dodecylsulfate in 0.01 N HCl to lyse the cells, and samples are incubated overnight. The absorbance at 590 nm is determined for each sample using a Molecular Devices microplate reader. Absorbance values for each set of wells is compared to assess viral control infection, uninfected control cell response as well as test compound by cytotoxicity and antiviral efficacy.

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in particular other strains of HIV, e.g. HIV-2, human T-cell leukemia virus, respiratory syncitial virus, simia immunodeficiency virus, feline leukemia virus, feline immuno-deficiency virus, hepadnavirus, cytomegalovirus and picornavirus. Thus, the subject compounds are effective in the treatment and/or proplylaxis of retroviral infections.

Compounds of the present invention can possess one or more asymmetric carbon atoms and are thus capable of existing in the form of optical isomers as well as in the form of racemic or nonracemic mixtures thereof. The optical. isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. water or oil-soluble or dispersible products are thereby obtained.

Examples of acids which may be employed to form pharmaceutically acceptable acid addition salts include such in organic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease; the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT, DDI, DDC or with glucosidase inhibitors, such as N-butyl-1-deoxynojirimycin or prodrugs thereof, for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound represented by the formula:

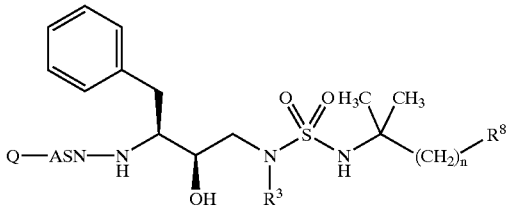

or a pharmaceutically acceptable salt or ester thereof, wherein n represents 0, 1, or 2;

$R^3$ represents a member selected from the group consisting of: alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, or thioalkyl, alkylthioalkyl or arylthioalkyl radicals and the sulfone or sulfoxide derivatives thereof; and $R^8$ represents a member selected from the group consisting of: cyano, hydroxyl, alkyl, alkoxy, cycloalkyl, aryl, aralkyl, heterocycloalky or heteroaryl radicals and radicals represented by the formulas $C(O)R^{16}$, $CO_2R^{16}$, $SO_2R^{16}$, $SR^{16}$, $CONR^{16}R^{17}$, $CF_3$ or $NR^{16}R^{17}$; and wherein $R^{16}$ and $R^{17}$ independently represent a member selected from the group consisting of: hydrogen and radicals as defined for $R^3$, or $R^{16}$ and $R^{17}$ together with a nitrogen to which they are attached in the formula $NR^{16}R^{17}$ represent heterocycloalkyl or heteroaryl radicals.

2. A compound of claim 1 or a pharmaceutically acceptable salt or ester thereof, wherein:

$R^3$ represents a member selected from the group consisting of: alkyl, aralkyl, or heteroaralkyl; and $R^8$ represents a member selected from the group consisting of: cyano, hydroxyl, aryl, and heteroaryl radicals and radicals represented by the formulas $C(O)R^{16}$, $CO_2R^{16}$, $SO_2R^{16}$, $SR^{16}$, $CONR^{16}R^{17}$, or $NR^{16}R^{17}$; and wherein $R^{16}$ and $R^{17}$ independently represent a member selected from the group consisting of: hydrogen, methyl, or phenyl, or $R^{16}$ and $R^{17}$ together with a nitrogen to which they are attached in the formula $NR^{16}R^{17}$ represent heterocycloalkyl and heteroaryl radicals.

3. A compound represented by the formula:

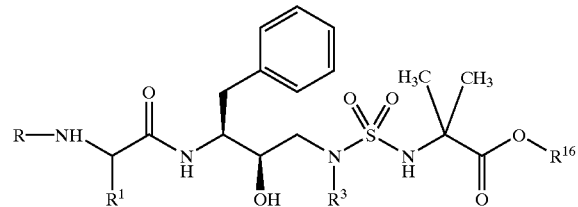

or a pharmaceutically acceptable salt or ester thereof, wherein:

R represents a member selected from the group consisting of: hydrogen, alkyl, alkenyl, alkynyl, cycloalkyl, aryl, aralkyl, alkoxycarbonyl, alkoxyalkyl, aryloxyalkyl, heteroaryloxyalkyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxy-carbonyl, heterocyclylalkanoyl, heterocyclylalkoxycarbonyl, heteroaralkanoyl, heteroaralkoxy-carbonyl, heteroaryloxycarbonyl, heteroaroyl, hydroxyalkyl, aminocarbonyl, aminoalkanoyl, and mono- or disubstituted aminocarbonyl and mono- or disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or wherein said aminocarbonyl or aminoalkanoyl radicals are disubstituted, said substituents along with the nitrogen atom to which they are attached form a heterocycloalkyl or heteroaryl radical;

$R^1$ represents a member selected from the group consisting of: hydrogen, $-CH_2C(O)NH_2$, $-CH_2SO_2NH_2$, $-CH_2CO_2CH_3$, $-CO_2CH_3$, $-CONH_2$, $-CH_2C(O)NHCH_3$, $-C(CH_3)_2(SH)$, $-C(CH_3)_2(SCH_3)$, $-C(CH_3)_2(S[O]CH_3)$, $-C(CH_3)_2(S[O]_2CH_3)$, alkyl, haloalkyl, alkenyl, alkynyl and cycloalkyl radicals, and amino acid side chains selected from asparagine, S-methyl cysteine or methionine and the sulfoxide (SO) or sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyanoalanine or valine side chains;

R³ represents a member selected from the group consisting of: alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- or disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical, and thioalkyl, alkylthioalkyl or arylthioalkyl radicals and the sulfone or sulfoxide derivatives thereof; and R¹⁶ represents a member selected from the group consisting of: hydrogen and radicals as defined for R³.

4. A compound of claim 3 or a pharmaceutically acceptable salt or ester thereof, wherein:

R represents a member selected from the group consisting of: benzyloxycarbonyl, N,N-dimethylglycine, or 2-quinolinylcarbonyl;

R¹ represents a member selected from the group consisting of: t-butyl, i-butyl, and —CH₂C(O)NH₂;

R³ represents a member selected from the group consisting of: i-amyl or i-butyl; and R¹⁶ represents a member selected from the group consisting of: hydrogen, methyl, ethyl, i-propyl, t-butyl, or benzyl.

5. A compound of claim 3 represented by the formula:

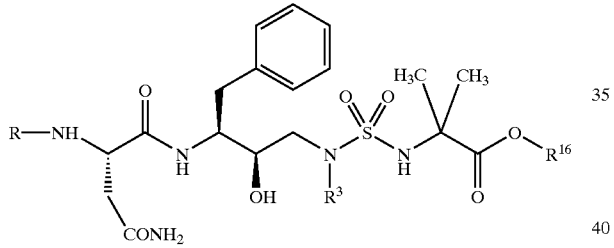

or a pharmaceutically acceptable salt or ester thereof, wherein:

R represents a member selected from the group consisting of: benzyloxycarbonyl, 2-quinolinylcarbonyl, or β-naphthylcarbonyl;

R³ represents a member selected from the group consisting of: methyl, i-propyl, t-butyl, i-butyl, n-butyl, i-amyl, n-pentyl, n-hexyl, cyclohexyl, phenyl, cyclohexylmethyl, or benzyl; and R¹⁶ represents a member selected from the group consisting of: hydrogen, methyl, ethyl, i-propyl, t-butyl, or benzyl.

6. A compound represented by the formula:

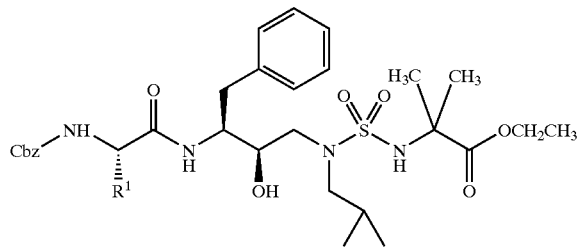

or a pharmaceutically acceptable salt or ester thereof, wherein:

R¹ represents a member selected from the group consisting of: hydrogen, —CH₂SO₂NH₂, —CH₂SO₂CH₃, —CH₂CO₂CH₃, —CO₂CH₃, —CONH₂, —CH₂C(O)NHCH₃, —C(CH₃)₂(SH), —C(CH₃)₂(SCH₃), —CH₂SCH₃, —C(CH₃)₂(S[O]CH₃), —C(CH₃)₂(S[O]₂CH₃), alkyl, haloalkyl, alkenyl, alkynyl and cycloalkyl radicals, and amino acid side chains selected from asparagine, S-methyl cysteine and methionine and the sulfoxide (SO) or sulfone (SO₂) derivatives thereof, isoleucine, allo-isoleucine, alanine, leucine, tert-leucine, phenylalanine, ornithine, histidine, norleucine, glutamine, threonine, glycine, allo-threonine, serine, O-alkyl serine, aspartic acid, beta-cyanoalanine or valine side chains.

7. A compound of claim 6 or a pharmaceutically acceptable salt or ester thereof, wherein:

R¹ represents a member selected from the group consisting of: —CH₂SO₂CH₃, —CH(OH)CH₃, —CH(CH₃)₂, —CH₂SOCH₃, —CH₂SO₂NH₂, —CH₂SCH₃, —CH₂CH(CH₃)₂, —CH₂CH₂C(O)NH₂, —CH₂C≡CH, —CH₂CH=CH₂, —C(CH₃)₂SCH₃, or —C(CH₃)₂SO₂CH₃.

* * * * *